US010029057B2

(12) United States Patent
Jafari et al.

(10) Patent No.: US 10,029,057 B2
(45) Date of Patent: *Jul. 24, 2018

(54) METHODS AND SYSTEMS FOR TRIGGERING WITH UNKNOWN BASE FLOW

(71) Applicant: Covidien LP, Boulder, CO (US)

(72) Inventors: Mehdi M. Jafari, Laguna Hills, CA (US); Rhomere S. Jimenez, Chula Vista, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 957 days.

This patent is subject to a terminal disclaimer.

(21) Appl. No.: 14/470,330

(22) Filed: Aug. 27, 2014

(65) Prior Publication Data

US 2014/0360497 A1 Dec. 11, 2014

Related U.S. Application Data

(63) Continuation of application No. 13/435,968, filed on Mar. 30, 2012, now Pat. No. 8,844,526.

(51) Int. Cl.
*A61M 16/00* (2006.01)
*A61M 16/20* (2006.01)
*A61M 16/08* (2006.01)

(52) U.S. Cl.
CPC .... *A61M 16/0003* (2014.02); *A61M 16/0051* (2013.01); *A61M 16/0063* (2014.02); *A61M 16/026* (2017.08); *A61M 16/204* (2014.02); *A61M 16/205* (2014.02); *A61M 16/0833* (2014.02); *A61M 2016/0021* (2013.01); *A61M 2016/0036* (2013.01); *A61M 2016/0039* (2013.01); *A61M 2016/0042* (2013.01); *A61M 2205/16* (2013.01); *A61M 2205/505* (2013.01); *A61M 2205/70* (2013.01)

(58) Field of Classification Search
CPC .......... A61M 16/0003; A61M 16/0063; A61M 16/204; A61M 16/205; A61M 16/0051; A61M 16/0833; A61M 2016/0021; A61M 2016/0036
See application file for complete search history.

(56) References Cited

U.S. PATENT DOCUMENTS 3,584,621 A 6/1971 Bird et al.
3,586,021 A 6/1971 McGuinness
3,633,576 A 1/1972 Gorsuch
(Continued)

FOREIGN PATENT DOCUMENTS

WO 2003055552 7/2003

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Gregory Anderson
*Assistant Examiner* — Jonathan Paciorek

(57) ABSTRACT

This disclosure describes systems and methods for providing novel back-up ventilation that allows the patient to trigger or initiate the delivery of breath. Further, this disclosure describes systems and methods for triggering ventilation when base flow is unknown or undeterminable by the ventilator.

19 Claims, 8 Drawing Sheets

(56) References Cited

U.S. PATENT DOCUMENTS

| | | |
|---|---|---|
| 3,662,751 A | 5/1972 | Barkalow et al. |
| 3,664,370 A | 5/1972 | Warnow |
| 3,669,108 A | 6/1972 | Sundblom et al. |
| 3,695,263 A | 10/1972 | Kipling |
| 3,741,208 A | 6/1973 | Jonsson et al. |
| 3,753,436 A | 8/1973 | Bird et al. |
| 3,756,229 A | 9/1973 | Ollivier |
| 3,768,468 A | 10/1973 | Cox |
| 3,789,837 A | 2/1974 | Philips et al. |
| 3,827,433 A | 8/1974 | Shannon |
| 3,834,382 A | 9/1974 | Lederman et al. |
| 3,869,771 A | 3/1975 | Bollinger |
| 3,889,669 A | 6/1975 | Weigl |
| 3,889,670 A | 6/1975 | Loveland et al. |
| 3,896,800 A | 7/1975 | Cibulka |
| 3,903,881 A | 9/1975 | Weigl |
| 3,905,362 A | 9/1975 | Eyrick et al. |
| 3,908,987 A | 9/1975 | Boehringer |
| 3,910,261 A | 10/1975 | Ragsdale et al. |
| 3,923,056 A * | 12/1975 | Bingmann .......... A61M 16/024 128/204.21 |
| 3,961,627 A | 6/1976 | Ernst et al. |
| 3,976,052 A | 8/1976 | Junginger et al. |
| 3,976,065 A | 8/1976 | Durkan |
| 3,981,301 A | 9/1976 | Warnow et al. |
| 4,003,377 A * | 1/1977 | Dahl ................. A61M 16/022 128/204.23 |
| 4,020,834 A | 5/1977 | Bird |
| 4,029,120 A | 6/1977 | Christianson |
| 4,044,763 A | 8/1977 | Bird |
| 4,050,458 A | 9/1977 | Friend |
| 4,057,059 A | 11/1977 | Reid, Jr. et al. |
| 4,060,078 A | 11/1977 | Bird |
| 4,082,093 A | 4/1978 | Fry et al. |
| 4,121,578 A | 10/1978 | Torzala |
| 4,155,357 A | 5/1979 | Dahl |
| 4,164,219 A | 8/1979 | Bird |
| 4,197,843 A | 4/1980 | Bird |
| 4,197,856 A | 4/1980 | Northrop |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,245,633 A | 1/1981 | Erceg |
| 4,265,237 A | 5/1981 | Schwanbom et al. |
| 4,267,827 A | 5/1981 | Racher et al. |
| 4,275,722 A | 6/1981 | Sorensen |
| 4,281,651 A | 8/1981 | Cox |
| 4,285,340 A | 8/1981 | Gezari et al. |
| 4,320,754 A | 3/1982 | Watson et al. |
| 4,323,064 A | 4/1982 | Hoenig et al. |
| 4,340,044 A | 7/1982 | Levy et al. |
| 4,351,328 A | 9/1982 | Bodai |
| 4,351,329 A | 9/1982 | Ellestad et al. |
| 4,351,344 A | 9/1982 | Stenzler |
| 4,401,115 A | 8/1983 | Monnier |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,596,246 A | 6/1986 | Lyall |
| 4,598,706 A | 7/1986 | Darowski et al. |
| 4,611,591 A | 9/1986 | Inui et al. |
| 4,612,928 A | 9/1986 | Tiep et al. |
| 4,622,976 A | 11/1986 | Timpe et al. |
| 4,640,277 A | 2/1987 | Meyer et al. |
| 4,648,407 A | 3/1987 | Sackner |
| 4,651,731 A | 3/1987 | Vicenzi et al. |
| 4,752,089 A | 6/1988 | Carter |
| 4,757,824 A | 7/1988 | Chaumet |
| 4,766,894 A | 8/1988 | Legrand et al. |
| 4,796,618 A | 1/1989 | Garraffa |
| 4,813,409 A | 3/1989 | Ismach |
| 4,821,709 A | 4/1989 | Jensen |
| 4,877,023 A | 10/1989 | Zalkin |
| 4,889,116 A | 12/1989 | Taube |
| 4,921,642 A | 5/1990 | LaTorraca |
| 4,924,862 A | 5/1990 | Levinson |
| 4,954,799 A | 9/1990 | Kumar |
| 4,981,295 A | 1/1991 | Belman et al. |
| 4,982,735 A | 1/1991 | Yagata et al. |
| 5,002,050 A | 3/1991 | McGinnis |
| 5,007,420 A | 4/1991 | Bird |
| 5,016,626 A | 5/1991 | Jones |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,737 A | 12/1991 | Goulding |
| 5,099,837 A | 3/1992 | Russel, Sr. et al. |
| 5,150,291 A | 9/1992 | Cummings et al. |
| 5,154,167 A | 10/1992 | Hepburn |
| 5,158,569 A | 10/1992 | Strickland et al. |
| 5,161,525 A | 11/1992 | Kimm et al. |
| 5,165,397 A | 11/1992 | Arp |
| 5,165,398 A | 11/1992 | Bird |
| 5,222,491 A | 6/1993 | Thomas |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,698 A | 4/1994 | Tobia et al. |
| 5,315,989 A | 5/1994 | Tobia |
| 5,316,009 A | 5/1994 | Yamada |
| 5,318,487 A | 6/1994 | Golen et al. |
| 5,319,540 A | 6/1994 | Isaza et al. |
| 5,323,772 A * | 6/1994 | Linden ................ A61M 16/024 128/204.21 |
| 5,325,861 A | 7/1994 | Goulding |
| 5,333,606 A | 8/1994 | Schneider et al. |
| 5,335,651 A | 8/1994 | Foster et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,458,137 A | 10/1995 | Axe et al. |
| 5,479,920 A | 1/1996 | Piper et al. |
| 5,487,383 A | 1/1996 | Levinson |
| 5,494,028 A | 2/1996 | DeVries et al. |
| 5,507,282 A | 4/1996 | Younes |
| 5,509,406 A | 4/1996 | Kock et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |

(56) References Cited

U.S. PATENT DOCUMENTS

| | | |
|---|---|---|
| 5,542,415 A | 8/1996 | Brady |
| 5,544,674 A | 8/1996 | Kelly |
| 5,549,106 A | 8/1996 | Gruenke et al. |
| 5,549,655 A | 8/1996 | Erickson |
| 5,551,419 A | 9/1996 | Froehlich et al. |
| 5,564,416 A | 10/1996 | Jones |
| 5,575,283 A | 11/1996 | Sjoestrand |
| 5,582,163 A | 12/1996 | Bonassa |
| 5,596,984 A | 1/1997 | O'Mahony et al. |
| 5,603,315 A | 2/1997 | Sasso, Jr. |
| 5,606,968 A | 3/1997 | Mang |
| 5,615,669 A | 4/1997 | Olsson et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,645,053 A | 7/1997 | Remmers et al. |
| 5,647,345 A | 7/1997 | Saul |
| 5,647,351 A | 7/1997 | Weismann et al. |
| 5,651,360 A | 7/1997 | Tobia |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,694,926 A | 12/1997 | DeVries et al. |
| 5,706,799 A | 1/1998 | Imai et al. |
| 5,715,812 A | 2/1998 | Deighan et al. |
| 5,720,277 A | 2/1998 | Olsson et al. |
| 5,727,562 A | 3/1998 | Beck |
| 5,730,122 A | 3/1998 | Lurie |
| 5,735,267 A | 4/1998 | Tobia |
| 5,738,090 A | 4/1998 | Lachmann et al. |
| 5,740,796 A | 4/1998 | Skog |
| 5,752,509 A | 5/1998 | Lachmann et al. |
| 5,762,480 A | 6/1998 | Adahan |
| 5,769,072 A | 6/1998 | Olsson et al. |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,868,133 A | 2/1999 | DeVries et al. |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,162 A | 8/1999 | Christian |
| 5,934,274 A | 8/1999 | Merrick et al. |
| 5,970,975 A | 10/1999 | Estes et al. |
| 5,975,081 A | 11/1999 | Hood et al. |
| 5,983,891 A | 11/1999 | Fukunaga |
| 6,000,396 A | 12/1999 | Melker et al. |
| 6,003,513 A | 12/1999 | Readey et al. |
| 6,010,459 A | 1/2000 | Silkoff et al. |
| 6,024,089 A | 2/2000 | Wallace et al. |
| 6,029,664 A | 2/2000 | Zdrojkowski et al. |
| 6,029,667 A | 2/2000 | Lurie |
| 6,041,780 A | 3/2000 | Richard et al. |
| 6,042,550 A | 3/2000 | Haryadi et al. |
| 6,044,841 A | 4/2000 | Verdun et al. |
| 6,047,860 A | 4/2000 | Sanders |
| 6,066,101 A | 5/2000 | Johnson et al. |
| 6,067,984 A | 5/2000 | Piper |
| 6,076,519 A | 6/2000 | Johnson |
| 6,076,523 A | 6/2000 | Jones et al. |
| 6,095,139 A | 8/2000 | Psaros |
| 6,095,140 A | 8/2000 | Poon et al. |
| 6,102,038 A | 8/2000 | DeVries |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,674 A | 9/2000 | Rich |
| 6,135,106 A | 10/2000 | Dirks et al. |
| 6,138,675 A | 10/2000 | Berthon-Jones |
| 6,142,150 A | 11/2000 | O'Mahoney |
| 6,148,814 A | 11/2000 | Clemmer et al. |
| 6,152,132 A | 11/2000 | Psaros |
| 6,158,432 A | 12/2000 | Biondi et al. |
| 6,158,433 A | 12/2000 | Ong et al. |
| 6,161,539 A | 12/2000 | Winter |
| 6,192,885 B1 | 2/2001 | Jalde |
| 6,200,271 B1 | 3/2001 | Kuck et al. |
| 6,210,342 B1 | 4/2001 | Kuck et al. |
| 6,213,119 B1 | 4/2001 | Brydon et al. |
| 6,217,524 B1 | 4/2001 | Orr et al. |
| 6,220,244 B1 | 4/2001 | McLaughlin |
| 6,220,245 B1 | 4/2001 | Takabayashi et al. |
| 6,230,708 B1 * | 5/2001 | Radko .................. A61M 16/00 128/200.24 |
| 6,238,351 B1 | 5/2001 | Orr et al. |
| 6,241,681 B1 | 6/2001 | Haryadi et al. |
| 6,258,038 B1 | 7/2001 | Haryadi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,305,374 B1 | 10/2001 | Zdrojkowski et al. |
| 6,306,098 B1 | 10/2001 | Orr et al. |
| 6,318,365 B1 * | 11/2001 | Vogele ................ A61M 16/024 128/204.18 |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,427,692 B1 | 8/2002 | Hoglund |
| 6,439,229 B1 | 8/2002 | Du et al. |
| 6,443,154 B1 | 9/2002 | Jalde et al. |
| 6,450,163 B1 | 9/2002 | Blacker et al. |
| 6,450,968 B1 | 9/2002 | Wallen et al. |
| 6,467,477 B1 | 10/2002 | Frank et al. |
| 6,467,478 B1 | 10/2002 | Merrick et al. |
| 6,510,846 B1 | 1/2003 | O'Rourke |
| 6,512,938 B2 | 1/2003 | Claure et al. |
| 6,526,970 B2 | 3/2003 | DeVries et al. |
| 6,532,957 B2 | 3/2003 | Berthon-Jones |
| 6,532,960 B1 | 3/2003 | Yurko |
| 6,537,228 B1 | 3/2003 | Lambert |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,557,553 B1 | 5/2003 | Borrello |
| 6,560,991 B1 | 5/2003 | Kotliar |
| 6,564,798 B1 | 5/2003 | Jalde |
| 6,568,387 B2 | 5/2003 | Davenport et al. |
| 6,571,795 B2 | 6/2003 | Bourdon |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,595,212 B1 | 7/2003 | Arnott |
| 6,601,583 B2 | 8/2003 | Pessala et al. |
| 6,609,517 B1 | 8/2003 | Estes et al. |
| 6,622,725 B1 | 9/2003 | Fisher et al. |
| 6,622,726 B1 | 9/2003 | Du |
| 6,626,175 B2 | 9/2003 | Jafari et al. |

(56) References Cited

U.S. PATENT DOCUMENTS

| | | |
|---|---|---|
| 6,640,806 B2 | 11/2003 | Yurko |
| 6,644,310 B1 | 11/2003 | Delache et al. |
| 6,659,100 B2 | 12/2003 | O'Rourke |
| 6,662,032 B1 | 12/2003 | Gavish et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,694,978 B1 | 2/2004 | Bennarsten |
| 6,705,314 B1 | 3/2004 | O'Dea |
| 6,718,974 B1 | 4/2004 | Moberg |
| 6,722,360 B2 | 4/2004 | Doshi |
| 6,725,447 B1 | 4/2004 | Gilman et al. |
| 6,739,337 B2 | 5/2004 | Isaza |
| 6,752,151 B2 | 6/2004 | Hill |
| 6,758,216 B1 | 7/2004 | Berthon-Jones et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg et al. |
| 6,786,216 B2 | 9/2004 | O'Rourke |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,848,444 B2 | 2/2005 | Smith et al. |
| 6,854,462 B2 | 2/2005 | Berthon-Jones et al. |
| 6,863,068 B2 | 3/2005 | Jamison et al. |
| 6,863,656 B2 | 3/2005 | Lurie |
| 6,866,040 B1 | 3/2005 | Bourdon |
| 6,877,511 B2 | 4/2005 | DeVries et al. |
| 6,899,103 B1 | 5/2005 | Hood et al. |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 6,986,349 B2 | 1/2006 | Lurie |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,032,589 B2 | 4/2006 | Kerechanin, II et al. |
| 7,036,504 B2 | 5/2006 | Wallace et al. |
| 7,040,318 B2 | 5/2006 | Däscher et al. |
| 7,056,334 B2 | 6/2006 | Lennox |
| 7,066,175 B2 | 6/2006 | Hamilton et al. |
| 7,066,177 B2 | 6/2006 | Pittaway et al. |
| 7,070,570 B2 | 7/2006 | Sanderson et al. |
| 7,077,131 B2 | 7/2006 | Hansen |
| 7,077,132 B2 | 7/2006 | Berthon-Jones |
| 7,080,646 B2 | 7/2006 | Wiesmann et al. |
| RE39,225 E | 8/2006 | Isaza et al. |
| 7,087,027 B2 | 8/2006 | Page |
| 7,089,932 B2 | 8/2006 | Dodds |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,104,962 B2 | 9/2006 | Lomask et al. |
| 7,117,438 B2 | 10/2006 | Wallace et al. |
| 7,121,277 B2 | 10/2006 | Ström |
| 7,122,010 B2 | 10/2006 | Böhm et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,156,095 B2 | 1/2007 | Melker et al. |
| 7,204,251 B2 | 4/2007 | Lurie |
| 7,211,049 B2 | 5/2007 | Bradley et al. |
| 7,219,666 B2 | 5/2007 | Friberg et al. |
| 7,246,618 B2 | 7/2007 | Habashi |
| 7,255,103 B2 | 8/2007 | Bassin |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,276,031 B2 | 10/2007 | Norman et al. |
| 7,278,962 B2 | 10/2007 | Lönneker Lammers |
| 7,290,544 B1 | 11/2007 | Särelä et al. |
| 7,296,573 B2 | 11/2007 | Estes et al. |
| 7,308,894 B2 | 12/2007 | Hickle |
| 7,311,668 B2 | 12/2007 | Lurie |
| 7,320,321 B2 | 1/2008 | Pranger et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,428,902 B2 | 9/2008 | Du et al. |
| 7,460,959 B2 | 12/2008 | Jafari |
| 7,465,275 B2 | 12/2008 | Stenqvist |
| 7,467,012 B1 | 12/2008 | Park et al. |
| 7,472,702 B2 | 1/2009 | Beck et al. |
| 7,478,634 B2 | 1/2009 | Jam |
| 7,481,222 B2 | 1/2009 | Reissmann |
| 7,487,773 B2 | 2/2009 | Li |
| 7,487,774 B2 | 2/2009 | Acker |
| 7,487,778 B2 | 2/2009 | Freitag |
| 7,527,058 B2 | 5/2009 | Wright et al. |
| RE40,814 E | 6/2009 | Van Brunt et al. |
| 7,547,285 B2 | 6/2009 | Kline |
| 7,552,731 B2 | 6/2009 | Jorczak et al. |
| 7,556,038 B2 | 7/2009 | Kirby et al. |
| 7,556,041 B2 | 7/2009 | Madsen |
| 7,562,657 B2 | 7/2009 | Blanch et al. |
| 7,574,368 B2 | 8/2009 | Pawlikowski et al. |
| 7,581,708 B2 | 9/2009 | Newkirk |
| 7,588,033 B2 | 9/2009 | Wondka |
| 7,617,824 B2 | 11/2009 | Doyle |
| 7,621,270 B2 | 11/2009 | Morris et al. |
| 7,628,151 B2 | 12/2009 | Bassin |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,682,312 B2 | 3/2010 | Lurie |
| 7,686,019 B2 | 3/2010 | Weiss et al. |
| 7,694,677 B2 | 4/2010 | Tang |
| 7,708,015 B2 | 5/2010 | Seeger et al. |
| 7,717,113 B2 | 5/2010 | Andrieux |
| 7,717,858 B2 | 5/2010 | Massad |
| 7,721,736 B2 | 5/2010 | Urias et al. |
| 7,722,546 B2 | 5/2010 | Madaus et al. |
| D618,356 S | 6/2010 | Ross |
| 7,730,884 B2 | 6/2010 | Sato et al. |
| 7,735,486 B2 | 6/2010 | Payne |
| 7,735,492 B2 | 6/2010 | Doshi et al. |
| 7,775,207 B2 | 8/2010 | Jaffe et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,810,498 B1 | 10/2010 | Patterson |
| 7,823,588 B2 | 11/2010 | Hansen |
| 7,841,347 B2 | 11/2010 | Sonnenschein et al. |
| 7,849,854 B2 | 12/2010 | DeVries et al. |
| 7,850,619 B2 | 12/2010 | Gavish et al. |
| 7,855,716 B2 | 12/2010 | McCreary et al. |
| 7,866,318 B2 | 1/2011 | Bassin |
| D632,796 S | 2/2011 | Ross et al. |
| D632,797 S | 2/2011 | Ross et al. |
| 7,886,739 B2 | 2/2011 | Soliman et al. |
| 7,891,354 B2 | 2/2011 | Farbarik |
| 7,893,560 B2 | 2/2011 | Carter |
| 7,909,034 B2 | 3/2011 | Sinderby et al. |

(56) References Cited

U.S. PATENT DOCUMENTS

| | | | |
|---|---|---|---|
| D638,852 S | 5/2011 | Skidmore et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,971,589 B2 | 7/2011 | Mashak et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,308 B2 | 9/2011 | Carlson et al. |
| 8,021,309 B2 | 9/2011 | Zilberg |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 8,844,526 B2 | 9/2014 | Jafari et al. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0004893 A1* | 6/2001 | Biondi ............... A61M 16/00 128/204.18 |
| 2002/0017301 A1 | 2/2002 | Lundin |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0117173 A1 | 8/2002 | Lynn et al. |
| 2002/0144681 A1 | 10/2002 | Cewers et al. |
| 2003/0029453 A1 | 2/2003 | Smith et al. |
| 2003/0140925 A1 | 7/2003 | Sapienza et al. |
| 2003/0168066 A1 | 9/2003 | Sallvin |
| 2003/0172929 A1 | 9/2003 | Muellner |
| 2003/0225339 A1 | 12/2003 | Orr et al. |
| 2004/0149282 A1 | 8/2004 | Hickle |
| 2004/0244804 A1 | 12/2004 | Olsen et al. |
| 2005/0034724 A1 | 2/2005 | O'Dea |
| 2005/0034727 A1 | 2/2005 | Shusterman et al. |
| 2005/0039748 A1 | 2/2005 | Andrieux |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0113668 A1 | 5/2005 | Srinivasan |
| 2005/0139212 A1 | 6/2005 | Bourdon |
| 2005/0166928 A1 | 8/2005 | Jiang |
| 2005/0247311 A1 | 11/2005 | Vacchiano et al. |
| 2005/0279358 A1 | 12/2005 | Richey, II |
| 2006/0021618 A1 | 2/2006 | Berthon-Jones et al. |
| 2006/0122662 A1 | 6/2006 | Tehrani et al. |
| 2006/0142815 A1 | 6/2006 | Tehrani et al. |
| 2006/0196507 A1 | 9/2006 | Bradley |
| 2006/0196508 A1 | 9/2006 | Chalvignac |
| 2006/0241708 A1 | 10/2006 | Boute |
| 2006/0249153 A1 | 11/2006 | DeVries et al. |
| 2006/0264762 A1 | 11/2006 | Starr |
| 2006/0272637 A1 | 12/2006 | Johnson |
| 2006/0283451 A1 | 12/2006 | Albertelli |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0056588 A1 | 3/2007 | Hayek |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0089741 A1 | 4/2007 | Bohm et al. |
| 2007/0123792 A1 | 5/2007 | Kline |
| 2007/0125377 A1 | 6/2007 | Heinonen et al. |
| 2007/0129646 A1 | 6/2007 | Heinonen et al. |
| 2007/0157931 A1 | 7/2007 | Parker et al. |
| 2007/0181122 A1 | 8/2007 | Mulier |
| 2007/0227537 A1 | 10/2007 | Bemister et al. |
| 2007/0272241 A1 | 11/2007 | Sanborn et al. |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0011296 A1 | 1/2008 | Schatzl |
| 2008/0021379 A1 | 1/2008 | Hickle |
| 2008/0033304 A1 | 2/2008 | Dalal et al. |
| 2008/0041383 A1 | 2/2008 | Matthews et al. |
| 2008/0045845 A1 | 2/2008 | Pfeiffer et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0135044 A1 | 6/2008 | Freitag et al. |
| 2008/0163872 A1 | 7/2008 | Negele et al. |
| 2008/0168990 A1 | 7/2008 | Cooke et al. |
| 2008/0178874 A1 | 7/2008 | Doshi et al. |
| 2008/0183057 A1 | 7/2008 | Taube |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0196720 A1 | 8/2008 | Kollmeyer et al. |
| 2008/0200775 A1 | 8/2008 | Lynn |
| 2008/0202525 A1 | 8/2008 | Mitton et al. |
| 2008/0202528 A1 | 8/2008 | Carter et al. |
| 2008/0208281 A1 | 8/2008 | Tehrani et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0283060 A1 | 11/2008 | Bassin |
| 2008/0295837 A1 | 12/2008 | McCormick et al. |
| 2008/0312519 A1 | 12/2008 | Maschke |
| 2008/0314385 A1 | 12/2008 | Brunner et al. |
| 2009/0007914 A1 | 1/2009 | Bateman |
| 2009/0013999 A1 | 1/2009 | Bassin |
| 2009/0020119 A1 | 1/2009 | Eger et al. |
| 2009/0038617 A1 | 2/2009 | Berthon-Jones et al. |
| 2009/0071478 A1 | 3/2009 | Kalfon |
| 2009/0090359 A1 | 4/2009 | Daviet et al. |
| 2009/0095297 A1 | 4/2009 | Hallett |

(56) References Cited

U.S. PATENT DOCUMENTS

| | | |
|---|---|---|
| 2009/0099621 A1 | 4/2009 | Lin et al. |
| 2009/0107982 A1 | 4/2009 | McGhin et al. |
| 2009/0114223 A1 | 5/2009 | Bonassa |
| 2009/0137919 A1 | 5/2009 | Bar-Lavie et al. |
| 2009/0139522 A1 | 6/2009 | Thomson et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0183739 A1 | 7/2009 | Wondka |
| 2009/0194109 A1 | 8/2009 | Doshi et al. |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0210032 A1 | 8/2009 | Beiski et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250058 A1 | 10/2009 | Lastow et al. |
| 2009/0260625 A1 | 10/2009 | Wondka |
| 2009/0266360 A1 | 10/2009 | Acker et al. |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0299155 A1 | 12/2009 | Yang et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308393 A1 | 12/2009 | Luceros |
| 2009/0308394 A1 | 12/2009 | Levi |
| 2009/0308398 A1 | 12/2009 | Ferdinand et al. |
| 2009/0314297 A1 | 12/2009 | Mathews |
| 2010/0011307 A1 | 1/2010 | Desfossez et al. |
| 2010/0016694 A1 | 1/2010 | Martin et al. |
| 2010/0018531 A1 | 1/2010 | Bassin |
| 2010/0024818 A1 | 2/2010 | Stenzler et al. |
| 2010/0024820 A1 | 2/2010 | Bourdon |
| 2010/0031443 A1 | 2/2010 | Georgiev et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078018 A1 | 4/2010 | Heinonen et al. |
| 2010/0078024 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0089396 A1 | 4/2010 | Richard et al. |
| 2010/0094366 A1 | 4/2010 | McCarthy |
| 2010/0101575 A1 | 4/2010 | Fedorko et al. |
| 2010/0108066 A1 | 5/2010 | Martin et al. |
| 2010/0108070 A1 | 5/2010 | Kwok |
| 2010/0114218 A1 | 5/2010 | Heath |
| 2010/0116270 A1 | 5/2010 | Edwards et al. |
| 2010/0125227 A1 | 5/2010 | Bird |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0148458 A1 | 6/2010 | Ross et al. |
| 2010/0175695 A1 | 7/2010 | Jamison |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252046 A1 | 10/2010 | Dahlström et al. |
| 2010/0258124 A1 | 10/2010 | Madaus et al. |
| 2010/0275920 A1 | 11/2010 | Tham et al. |
| 2010/0275921 A1 | 11/2010 | Schindhelm et al. |
| 2010/0282259 A1 | 11/2010 | Figueiredo et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0307507 A1 | 12/2010 | Li et al. |
| 2010/0319691 A1 | 12/2010 | Lurie et al. |
| 2010/0326442 A1 | 12/2010 | Hamilton et al. |
| 2010/0326447 A1 | 12/2010 | Loomas et al. |
| 2010/0331877 A1 | 12/2010 | Li et al. |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0017214 A1 | 1/2011 | Tehrani |
| 2011/0023875 A1 | 2/2011 | Ledwith |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0036352 A1 | 2/2011 | Estes et al. |
| 2011/0041849 A1* | 2/2011 | Chen .................. A61B 5/14551 128/204.23 |
| 2011/0041850 A1 | 2/2011 | Vandine et al. |
| 2011/0061650 A1 | 3/2011 | Heesch |
| 2011/0073112 A1 | 3/2011 | DiBlasi et al. |
| 2011/0088697 A1 | 4/2011 | DeVries et al. |
| 2011/0092841 A1 | 4/2011 | Bassin |
| 2011/0100365 A1 | 5/2011 | Wedler et al. |
| 2011/0108041 A1 | 5/2011 | Sather et al. |
| 2011/0112424 A1 | 5/2011 | Kesselman et al. |
| 2011/0112425 A1 | 5/2011 | Muhlsteff et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |

(56) References Cited

U.S. PATENT DOCUMENTS

| | | |
|---|---|---|
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209706 A1 | 9/2011 | Truschel et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0114115 A1 | 4/2016 | Glenn et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Hari, "Flow Sensor Fault Causing Ventilator Malfunction", Anaesthesia, 2005, 60, pp. 1042-2052; http://onlinelibrary.wiley.com/doi/10.1111/j.1365-2044.2005.04396.x/pdf; Accessed Jan. 16, 2015.

\* cited by examiner

METHODS AND SYSTEMS FOR TRIGGERING WITH UNKNOWN BASE FLOW

CROSS-REFERENCE TO RELATED APPLICATIONS

This application is a continuation application of U.S. patent application Ser. No. 13/435,968, entitled "METHODS AND SYSTEMS FOR TRIGGERING WITH UNKNOWN BASE FLOW," filed on Mar. 30, 2012, now issued U.S. Pat. No. 8,844,526, the entire disclosure of which is hereby incorporated herein by reference.

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes.

Triggering with Unknown Base Flow

This disclosure describes systems and methods for providing novel back-up ventilation that allows the patient to trigger or initiate the delivery of breath. Further, this disclosure describes systems and methods for triggering ventilation when base flow is unknown or undeterminable by the ventilator.

In part, this disclosure describes a method for ventilating a patient with a ventilator. The method includes:
 a) delivering a fixed base flow that is undeterminable;
 b) monitoring a windowed differential lung volume during exhalation;
 c) determining that the windowed differential lung volume is at about zero after a decreasing trend toward zero; and
 c) triggering inspiration based on the first of at least one of the following events to occur:
  i) a net negative change in lung volume with increasing magnitude is detected that is greater than an inspiratory trigger threshold directly after the step of determining that the windowed differential lung volume is about zero; and
  ii) a predetermined amount of time expires.

Additionally, this disclosure describes a method for ventilating a patient with a ventilator. The method includes:
 a) delivering a fixed base flow that is undeterminable;
 b) determining a stable portion of exhalation;
 c) monitoring an exhalation flow during the stable portion of exhalation;
 d) estimating a base flow based on the exhalation flow monitored during the stable portion of exhalation; and
 e) triggering inspiration based on the first of at least one of the following events to occur:
  i) a flow derivation based on the estimated base flow is detected that is greater than an inspiratory trigger threshold during the stable portion of exhalation; and
  ii) expiration of a predetermined amount of time.

The disclosure further describes a ventilator system that includes: a pressure generating system adapted to generate a flow of breathing gas; a ventilation tubing system including a patient interface for connecting the pressure generating system to a patient; at least one sensor operatively coupled to at least one of the pressure generating system, the patient, and the ventilation tubing system; a lung volume module for monitoring a windowed differential lung volume during exhalation and for determining when the windowed differential lung volume is at about zero after a decreasing trend toward zero; and a trigger module for triggering inspiration based on the first of at least one of the following events to occur 1) a net negative change in lung volume with increasing magnitude is detected directly after the lung volume module determines that the windowed differential lung volume is about zero that is greater than an inspiratory trigger threshold, and 2) a predetermined amount of time expires. The pressure generating system delivers an undeterminable fixed base flow.

The disclosure further describes a ventilator system that includes: a pressure generating system adapted to generate a flow of breathing gas; a ventilation tubing system including a patient interface for connecting the pressure generating system to a patient; at least one sensor operatively coupled to at least one of the pressure generating system, the patient, and the ventilation tubing system; a base flow estimator module for determining a stable portion of exhalation, monitoring the exhalation flow during the stable portion of exhalation based on the output, and for estimating a base flow based on the exhalation flow monitored during the stable portion of exhalation; and a trigger module for triggering inspiration based on the first of at least one of the following events to occur 1) a flow derivation based on an estimated base flow is detected that is greater than an inspiratory trigger threshold, and 2) a predetermined amount of time expires. The pressure generating system delivers an undeterminable fixed base flow. The at least one sensor is capable of generating an output indicative of an exhalation flow The disclosure additionally describes a computer-readable medium having computer-executable instructions for performing a method for ventilating a patient with a ventilator. The method includes:
 a) repeatedly delivering a fixed base flow that is undeterminable;
 b) repeatedly monitoring a windowed differential lung volume during exhalation;
 c) repeatedly determining that the windowed differential lung volume is at about zero after a decreasing trend toward zero; and
 d) repeatedly triggering inspiration based on the first of at least one of the following events to occur:
  i) a net negative change in lung volume with increasing magnitude is detected that is greater than an inspiratory trigger threshold directly after the step of determining that the windowed differential lung volume is about zero; and
  ii) a predetermined amount of time expires.

The disclosure also describes a ventilator system including means for delivering a fixed base flow that is undeterminable; means for monitoring a windowed differential lung volume during exhalation; means for determining that the windowed differential lung volume is at about zero after a decreasing trend toward zero; and means for triggering inspiration based on the first of at least one of the following events to occur 1) a net negative change in lung volume with increasing magnitude is detected that is greater than an inspiratory trigger threshold directly after the step of determining that the windowed differential lung volume is about zero and 2) a predetermined amount of time expires.

The disclosure additionally describes a computer-readable medium having computer-executable instructions for performing a method for ventilating a patient with a ventilator. The method includes:

a) repeatedly delivering a fixed base flow that is undeterminable;

b) repeatedly determining a stable portion of exhalation;

c) repeatedly monitoring an exhalation flow during the stable portion of exhalation;

d) repeatedly estimating a base flow based on the exhalation flow monitored during the stable portion of exhalation; and e) repeatedly triggering inspiration based on the first of at least one of the following events to occur:

i) a flow derivation based on the estimated base flow is detected that is greater than an inspiratory trigger threshold during the stable portion of exhalation; and ii) expiration of a predetermined amount of time.

The disclosure also describes a ventilator system including means for means for delivering a fixed base flow that is undeterminable; means for determining a stable portion of exhalation; means for monitoring an exhalation flow during the stable portion of exhalation; means for estimating a base flow based on the exhalation flow monitored during the stable portion of exhalation; and means for triggering inspiration based on the first of at least one of the following events to occur 1) a flow derivation based on the estimated base flow is detected that is greater than an inspiratory trigger threshold during the stable portion of exhalation and 2) expiration of a predetermined amount of time.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims.

DETAILED DESCRIPTION

Figure 1A:
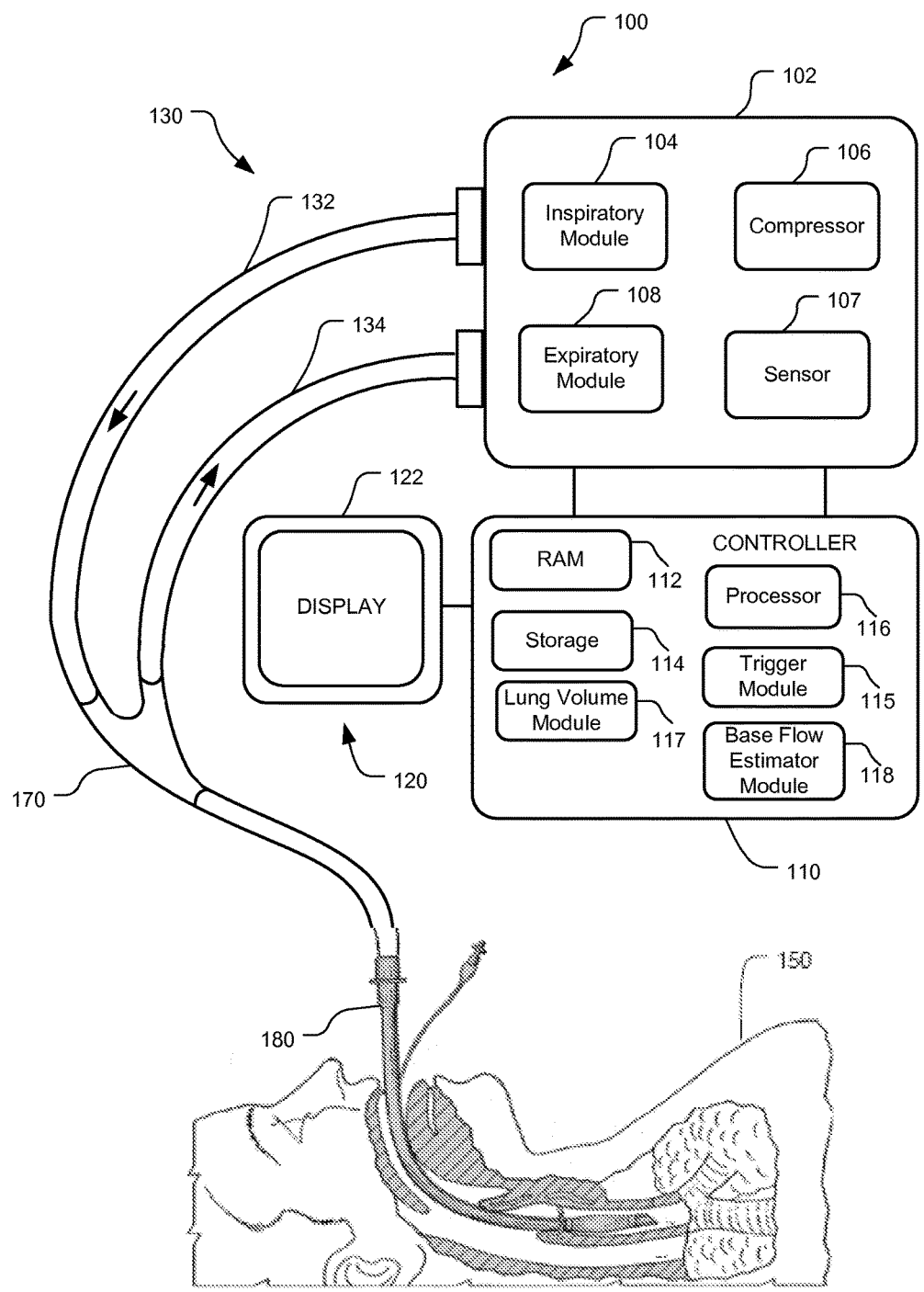
FIG. 1A illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes. Assist control modes allow a spontaneously breathing patient to trigger inspiration during ventilation.

The response performance of a medical ventilator to a patient trigger from exhalation into inhalation phase represents an important characteristic of a medical ventilator. A ventilator's trigger response impacts the patient's work of breathing and the overall patient-ventilator synchrony. The trigger response performance of a ventilator is a function of a patient's inspiratory behavior (breathing effort magnitude and timing characteristics) as well as the ventilator's gas delivery dynamics and flow control parameters (actuator response, dead bands, etc.).

In conventional flow triggering modes, a patient's inspiratory trigger is detected based on the magnitude of flow deviations generated by the patient's inspiratory effort. In a flow triggering mode, the ventilator delivers a fixed base flow during the exhalation phase. Accordingly, flow deviations are sensed by the computation of the ventilator net flow (base flow-exhausted flow) and compared against a set trigger threshold for triggering.

Base flow is the delivered flow during exhalation and consists of a desired combination of appropriate gases. A fixed base flow may be generated by a controller regulating an actuator (valve) to maintain a constant desired flow rate from a regulated pressurized gas source into the ventilator circuit. The magnitude or the flow rate generated by the regulator at different open positions is determined by an inspiratory flow sensor. Therefore, base flow is determined by the ventilator by measuring the amount of flow delivered to the patient via an inspiration flow sensor during exhalation.

Exhausted flow is measured during the expiratory phase of a ventilator breath while a base flow is delivered through the patient circuit. To determine the volume of gas exhaled by the patient, the net flow (total delivered flow minus total flow through exhalation module) is used for integration. That is, the delivered base flow is subtracted from the sum of the base flow and patient flow exiting through the exhalation port. The flow exiting the exhalation module during the active phase of patient exhalation is the sum of base flow delivered by the ventilator and exhaled flow from the patient lung.

In the absence of an inspiratory flow sensor or under fault conditions when an inspiratory flow sensor may not be utilized, a fixed base flow may be generated by opening the delivery valve or regulator to a fixed position. However, the magnitude of the generated base flow is undeterminable, so a conventional flow triggering algorithm cannot be used to compare the net flow (base flow-exhausted flow) against the trigger threshold. Accordingly, patient initiated triggers cannot be detected and prevent the use of a spontaneous mode of ventilation.

An example of a fault condition is presented by the Back-Up Ventilation (BUV) mode under which the data measurement and acquisition subsystem on the delivery side of the ventilator is deactivated because of a malfunction. Conventional ventilators declare an alarm and terminate ventilation. However, the BUY mode allows a ventilator to continue ventilating the patient under such conditions until an appropriate substitute device is made available. However, currently, the BUV mode does not allow for spontaneously breathing patients to trigger ventilation. Therefore, the BUV mode is uncomfortable for spontaneously breathing patients.

Accordingly, the systems and methods described herein provide for a triggering mechanism when a fixed base flow is undeterminable by the ventilator. As used herein, a base flow is undeterminable by the ventilator when the base flow delivered is not measureable in the inhalation limb of the ventilator tubing system. The capability of triggering without the knowledge of a flow rate for a fixed base flow allows a BUV mode to maintain comfortable patient-ventilator synchrony. The systems and methods described herein provide two different mechanisms of triggering for a spontaneous patient when the ventilator cannot determine the base flow.

During the first mechanism, a windowed differential lung volume comparison is utilized along with a progressive monitoring of differential volume changes into and out of the patient lung over a certain time window. By using the volume differential over windowed intervals, the sum of the fixed base flow rate cancels out and there is no need to have a measurement for delivered base flow in order to determine a patient-trigger for inspiration.

During the second mechanism, the ventilator monitors exhalation flow during a stable portion of exhalation. The ventilator utilizes the exhalation flow measurements during the stable portion of exhalation to determine an estimated base flow. The estimated base flow is substituted for the actual base flow allowing the traditional flow triggering algorithm to be utilized. For example, the ventilator is able to determine flow deviations by the computation of the ventilator net flow (base flow-exhausted) which is compared against a set trigger threshold for triggering.

Figure 1B:
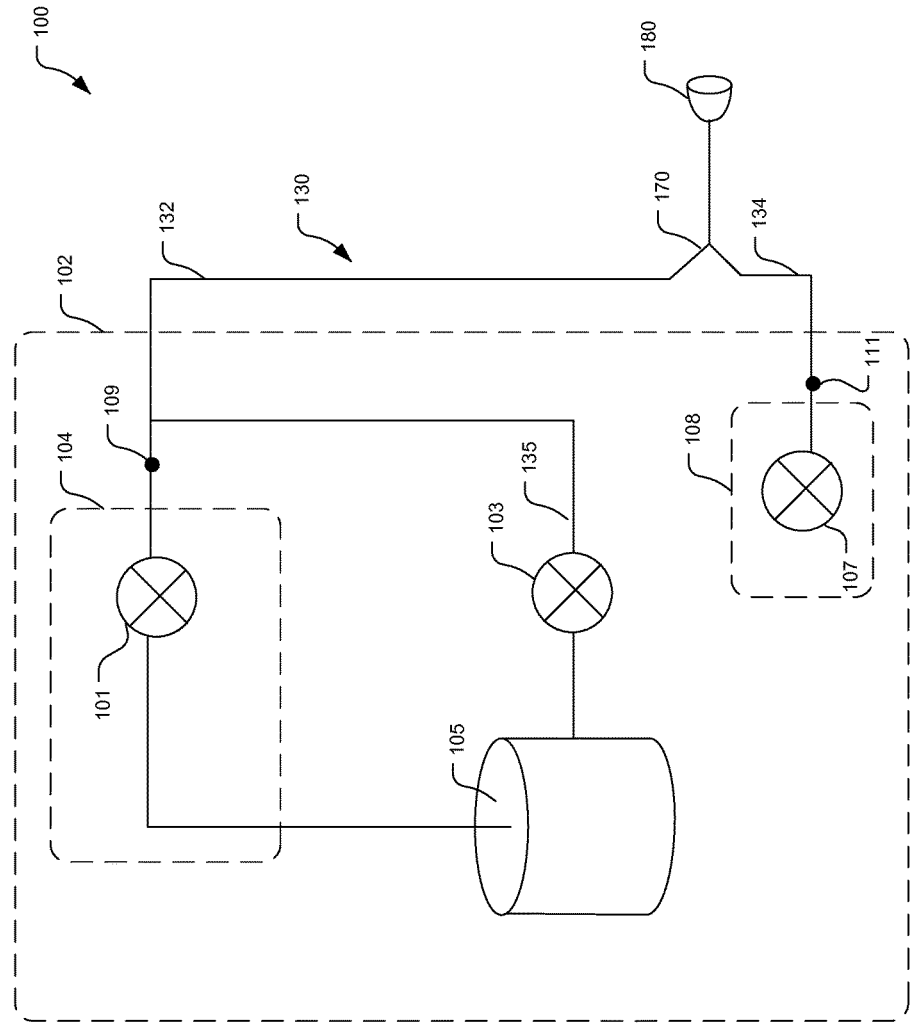
FIG. 1B illustrates an embodiment of a ventilator.

FIGS. 1A and 1B are diagrams illustrating an embodiment of an exemplary ventilator 100. The exemplary ventilator 100 illustrated in FIG. 1A is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106, accumulator 105 and/or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory valve 101 for controlling gas delivery to the patient 150 and/or gas delivery through the inspiratory limb 132. In some embodiments, inspiratory module 104 is configured to provide ventilation according to various ventilator modes, such as mandatory and assist modes.

The expiratory module 108 is configured to release gases from the patient's lungs according to prescribed ventilatory settings. The expiratory module 108 is associated with and/or controls an expiratory valve 107 for releasing gases from the patient 150. Further, the expiratory module 108 and/or the inspiratory module 104 may instruct the pressure generating system 102 and/or the inspiratory module 104 to deliver a base flow during exhalation. In an alternative embodiment, the pressure generating system 102 may instruct the inspiratory module 104 to deliver a base flow during exhalation.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1A illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, trigger module 115, lung volume module 117, base flow estimator module 118, and any other suitable components and/or modules. In one embodiment, sensors 107 generate output and send this output to pneumatic system 102, other sensors 107, expiratory module 108, inspiratory module 104, processor 116, controller 110 trigger module 115, lung volume module 117, base flow estimator module 118, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules 104, 108 for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Any sensory device useful for monitoring changes in measurable parameters during ventilatory treatment may be employed in accordance with embodiments described herein.

For example, in some embodiments, the one or more sensors 107 of the ventilator 100 include an inspiratory flow sensor 109 and an expiratory flow sensor 111 as illustrated in FIG. 1B. In one embodiment, the inspiratory flow sensor 109 is located in the inspiratory limb 132 and is controlled by the inspiratory module 104. However, the inspiratory flow sensor 109 may be located in any suitable position for monitoring inspiratory flow and may be monitored by any suitable ventilator component, such as a pressure generating system 102. In one embodiment, the expiratory flow sensor 111 is located in the expiratory limb 134 and is monitored by the expiratory module 108. However, the expiratory flow sensor 111 may be located in any suitable position for monitoring expiratory flow and may be monitored by any suitable ventilator component, such as a pressure generating system 102.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships.

The pneumatic system 102 may include a variety of other components, including mixing modules, valves, tubing, accumulators 105, filters, etc. In the event that the inspiratory module 104 malfunctions, in one embodiment, the pressure generating system 102 may instruct an accumulator 105 to deliver inspiratory flow and/or base flow through a bypass limb 135 and a back-up valve 103 to the ventilation tubing system 130, as illustrated in FIG. 111. In some embodiments, the bypass limb 135 is tubing that connects the pressure generating system 102 to the patient 150 and the exhalation limb 134 while bypassing the inspiratory module 104 and/or the inspiratory flow sensor 109. The back-up valve 103 is a valve that controls the flow of gas through the bypass limb 135. In some embodiments, the bypass limb 135 is a portion of the ventilation tubing system 130.

In some embodiments, when the inspiratory module 104 malfunctions, so too does the inspiratory flow sensor 109. In other embodiments, the delivered flow does not pass by and/or through the inspiratory flow sensor 109 during an inspiratory module 104 malfunction as illustrated in FIG. 1B. Accordingly, during some malfunctions, the delivered flow is not measured or is not accurately measured by an inspiratory flow sensor 109. In other embodiments, the ventilator 100 does not contain an inspiratory flow sensor 109.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate a WDLV, a net negative change in lung volume, an estimated base flow, an exhalation flow, a restricted period, a trigger threshold, a sampling period for the WDLV and/or any other information known, received, or stored by the ventilator 100.

In some embodiments, controller 110 includes memory 112, one or more processors 116, storage 114, and/or other components of the type commonly found in command and control computing devices. Controller 110 may further include a trigger module 115, lung volume module 117, and base flow estimator module 118, as illustrated in FIG. 1. In alternative embodiments, the trigger module 115, lung volume module 117, and base flow estimator module 118 are located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The base flow estimator module 118 determines an estimated base flow when a fixed base flow is indeterminable by the ventilator 100. In some embodiments, a fixed base flow is indeterminable by the ventilator 100 when at least one of the following conditions occur: an absence of an inspiratory flow sensor 109; a malfunction of the inspiratory flow sensor 109; a malfunction that prevents utilization of the inspiratory flow sensor 109; an inspiratory module 104 malfunction; a malfunction that deactivates at least one of a data measurement subsystem and a data acquisition subsystem, and any other ventilator malfunction that prevents the ventilator 100 from being able to measure inspiration flow. In some embodiments, during a malfunction, the ventilator 100 is capable of delivering a fixed base flow by holding the back-up valve 103 open in a fixed position; however, the amount of fixed base flow delivered cannot be determined by the ventilator 100, such as in a back-up ventilation.

Figure 5:
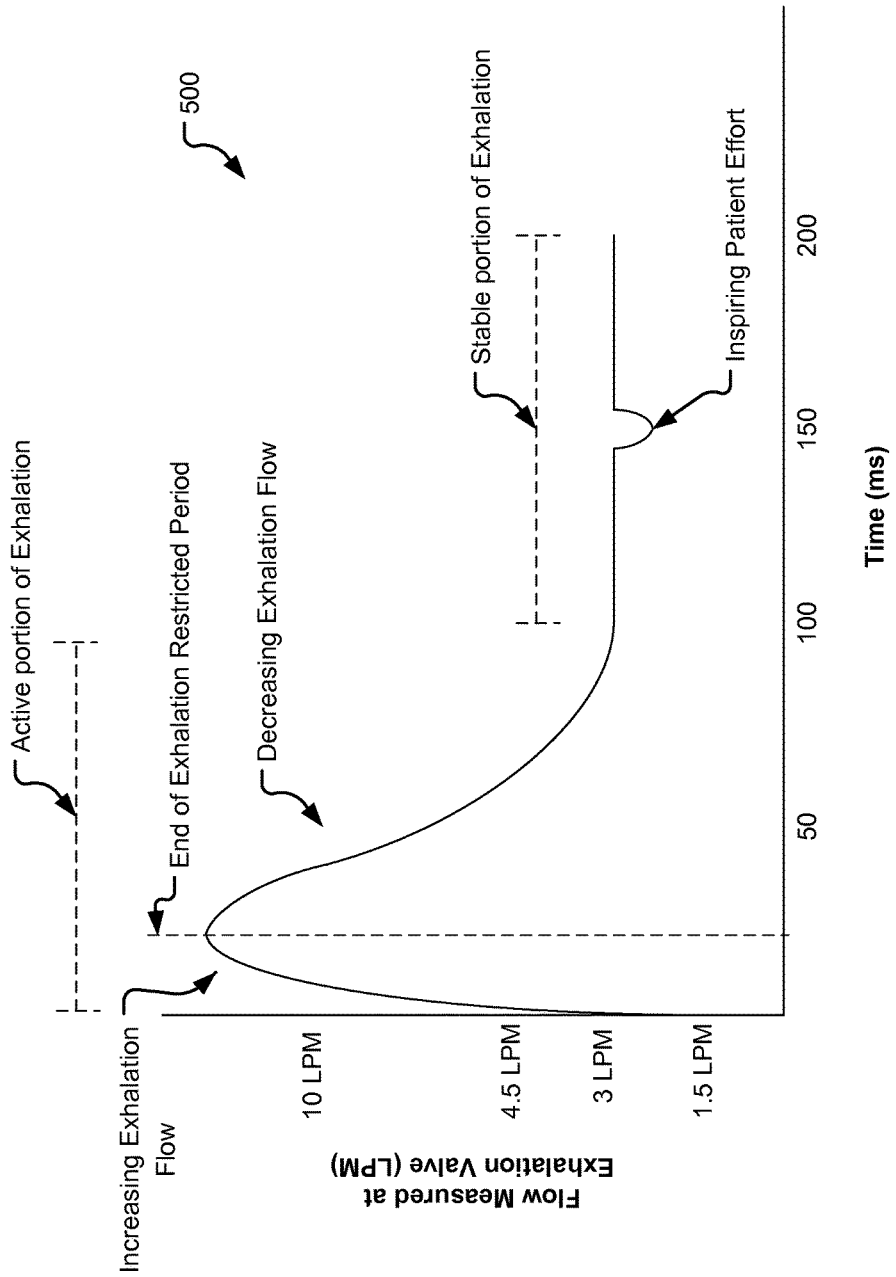
FIG. 5 illustrates an embodiment of a graph of an exhalation flow during one breath while ventilating a patient on a ventilator.

The base flow estimator module 118 determines an estimated base flow by monitoring exhalation flow during a stable portion of exhalation. The ventilator 100 must determine the stable portion of exhalation. In one embodiment, the stable portion of exhalation is the portion of exhalation when a patient 150 is contributing very little or no flow through the expiratory limb 134 and is prior to the beginning of inspiration as illustrated in FIG. 5. FIG. 5 illustrates an embodiment of a graph 500 of an exhalation flow during one breath while ventilating a patient 150 on a ventilator 100. In another embodiment, the ventilator 100 simulates a stable portion of exhalation during a transition period in the ventilator tubing system 130. The transition period is a short interval from the detection of a malfunction (e.g., inoperable flow sensor) until the start of a back-up ventilation mode, such as BUV. The ventilator simulates a stable portion of exhalation during this transition period by opening the exhalation valve fully and commanding the accumulator pressure to the fixed pressure level used during the back-up ventilation mode.

If the ventilator 100 simulates a stable portion of exhalation in the ventilator tubing system 130, the base flow estimator module 118 starts to measure exhalation flow one second after the start of the transition period. The ventilator knows exactly when the transition period begins because the transition period is controlled and/or determined by the ventilator 100. During this embodiment, after ensuring flow and pressure stability, the base flow estimator module 118 estimates base flow by taking a predetermined number of exhalation flow measurements and then averaging the exhalation flow measurements. In one embodiment, the base flow estimator module 118 measures exhalation flow and pressure in two 10-slot circular buffers. The averaged estimated flow measurement is then utilized as the estimated base flow by the base flow estimator module 118. During the ventilator simulated stable portion of exhalation, the pressure in the accumulator 105 is also measured to determine an estimated accumulator pressure. The base flow estimator module 118 sends the estimated base flow to the trigger module 115 to update the estimated base flow for use by the trigger module 115. In some embodiments, the estimated base flow determined during the transition period is the first estimated based flow to be utilized by the ventilator 100 to initialize a back-up ventilation mode. Accordingly, at the end of the transition period, the ventilator 100 starts the back-up ventilation mode.

When the ventilator 100 does not simulate the stable portion of exhalation, the base flow estimator module 118 must determine when the stable portion of exhalation occurs. In order to determine the stable portion of exhalation, the ventilator 100 monitors exhalation pressure and exhalation flow. In one embodiment, the exhaled flow and/or pressure is monitored with an expiratory flow sensor 111. In some embodiments, the exhaled flow and/or pressure is monitored with an exhalation pressure sensor 107.

In some embodiments, the base flow estimator module 118 collects multiple exhalation pressure and exhalation flow readings in at least two different circular buffers for a set period during exhalation after the expiration of a restricted period. The restricted period as used herein is a predetermined time period that starts at the beginning of exhalation. A patient 150 is prevented from triggering ventilation during the predetermined time period of the restricted period. For example, the restricted period may be 25 ms, 50 ms, 100 ms, and/or any other suitable time period for preventing a patient 150 from triggering inspiration.

In one embodiment, base flow estimator module 118 measures exhalation flow and pressure in two 10-slot circular buffers beginning one second after the end of the restricted period. In this embodiment, to determine stability, the base flow estimator module 118 may monitor the exhalation flow every computation cycle. In some embodiments, the computational cycle is every 5 ms. Next, during this embodiment, the base flow estimator module 118 determines if the difference between the maximum exhalation pressure and the minimum exhalation pressure is less that 1.5 cm of $H_2O$ ($(Max(P_e)-Min(P_e))<1.5$ cm $H_2O$) and determines if the difference between maximum exhalation flow and minimum exhalation flow is less than 1.5 LPM (($Max(Q_e)-Min(Q_e))<1.5$ LPM) during a certain interval. In this embodiment, the maximum and minimum values are calculated and compared based on the flow and pressure data saved in the 10-point buffer (pertaining to a 50 ms time period) after the initial exhalation restricted period has elapsed. Maximum and minimum values for the moving 10-point windows are tracked each computation cycle during exhalation. If the difference between the maximum exhalation pressure and the minimum exhalation pressure is less that 1.5 cm of $H_2O$ and the difference between maximum exhalation flow and minimum exhalation flow is less than 1.5 LPM, then the base flow estimator module 118 determines that the patient 150 is in the stable portion of exhalation (or when active exhalation has been completed) and calculates and updates an estimated base flow. If the difference between the maximum exhalation pressure and the minimum exhalation pressure is not less than 1.5 cm of $H_2O$ and/or the difference between maximum exhalation flow and minimum exhalation flow is not less than 1.5 LPM for either computation cycle, then the base flow estimator module 118 determines that the patient 150 is not in the stable portion of exhalation and does not calculate and update the estimated base flow.

The minimum pressure and flow values of 1.5 are based on the characteristics of an exemplary ventilator. Other values and different pressure and flow levels may be used as appropriate based on the ventilator being currently utilized. Further, depending on the utilized ventilator, the flow and pressure stability thresholds may not necessarily have the same magnitude. The thresholds are selected to provide minimal respiratory activity by the patient.

During this embodiment, the base flow estimator module 118 estimates a base flow by taking the last or most recently measured circular buffer and averaging all of the exhalation flows. For example, if the base flow estimator module 118 utilized a 10-slot circular buffer, the last ten exhalation flow are summed and then divided by ten providing an averaged exhalation flow. The base flow estimator module 118 utilizes the determined averaged exhalation flow as the estimated base flow. The base flow estimator module 118 sends the estimated base flow to the trigger module 115 to update the estimated base flow for use by the trigger module 115.

The embodiments, discussed above are merely exemplary and are not meant to be limiting. Any suitable method for determining a stable period of exhalation may be utilized by the present disclosure. In some embodiments, the base flow estimator module 118 continuously updates the estimated base flow during exhalation throughout ventilation with an undeterminable fixed base flow.

The lung volume module 117 monitors a windowed differential lung volume (WDLV) and determines a net negative change in lung volume with an increasing magnitude after a specific set of changes in the WDLV are detected. This lung volume module 117 utilizes a WDLV comparison to determine a progressive monitoring of differential volume changes into and out of the patient lung over a certain time window. By using the volume differential over windowed intervals, the sum of the fixed base flow rates cancel out as shown in the equations below:

$$WDLV = \Sigma_{j=n-i}^{j=n}(Qe(j)-Qd(j)) - \Sigma_{j=n-2i-1}^{j=n-i-1}(Qe(j)-Qd(j));$$

Therefore $$WDLV = \Sigma_{j=n-i}^{j=n}(Qe(j)) - \Sigma_{j=n-2i-1}^{j=n-i-1}(Qe(j))$$

and $$\Delta LV = WDLV * \Delta T.$$

WDLV=Differential Lung Volume over a window (w);
Qe=exhausted flow rate reading;
Qd=fixed delivered Base Flow;
n=discrete data sampling cycle number;
ΔLV=Differential lung volume;
w=window size; and
ΔT=sampling period (sec).
Because the fixed base flow rate cancels out there is no need to measure delivered flow or have an inspiratory flow sensor 109. For example, for a ventilator 100 with a data sampling rate of 200 HZ (5 ms Computation cycles), a window of 5 cycles (25 ms) may be used (w=5, i=4).

The WDLV will have a positive magnitude (or slope) with an increasing trend during the initial phase of active exhalation as the patient's exhaled flow increases to its peak as illustrated in FIG. 5. As the exhaled flow starts decreasing after passing through its peak, the WDLV metric inflects and will have a negative magnitude (or slope) and demonstrate a decreasing trend toward zero as active exhalation is completed as illustrated in FIG. 5. As used herein, an increasing trend occurs when the WDLV metric increases every cycle for at least three cycles resulting in a positive slope. As used herein, a decreasing trend occurs when the WDLV metric decreases every cycle for at least three cycles resulting in a negative slope.

The WDLV metric will be zero when the patient 150 has finished exhalation and therefore the flow rate exiting the exhalation module would represent the delivered base flow (under no leak condition). Accordingly, the lung volume module 117 can determine when the patient 150 has finished exhaling by monitoring when the WDLV metric reaches zero or about zero directly after a decreasing trend. A trend is at about zero when the trend is within a threshold. The threshold may be predetermined, user-selected, ventilator determined based on input parameters, or a set default. Any suitable threshold may be utilized by the ventilator 100 as long the threshold is indicative of a stable portion of exhalation by the patient 150.

If the lung volume module 117 determines that the WDLV metric is not about zero after a decreasing trend, then the lung volume module 117 continues to monitor the patient's lung volume until a WDLV metric of about zero or zero is detected or until inspiration is delivered by the ventilator 100. If the lung volume module 117 determines that the WDLV metric is at zero or about zero (i.e., when the patient has finished exhaling), the lung volume module 117 monitors for patient inspiratory effort. In some embodiments, the lung volume module 117 determines that the WDLV metric is at zero or about zero after an increasing WDLV trend followed by a decreasing trend in WDLV.

If the patient 150 initiates an inspiratory effort, a portion of the fixed base flow will move into the lung and the magnitude of the output flow reading (Qe) will decrease as illustrated in FIG. 5. Therefore, WDLV or ΔLV will indicate a net negative volume with increasing magnitude (−ΔLV=net volume into the lung (assigned a negative sign by convention)). As discussed above a ΔLV is equal to the WDLV (flow sum differential) multiplied by cycle time differential to provide the volume differential. Accordingly, the lung volume module 117 will monitor for a net negative volume with increasing magnitude during the portion of exhalation in which the lung volume module 117 determines that the WDLV metric is at zero or about zero. If the lung volume module 117 determines a net negative volume with increasing magnitude, the lung volume module 117 sends the net negative volume with increasing magnitude to the trigger module 115 and continues to monitor for additional net negative volume changes with increasing magnitude until an inspiration is delivered by the ventilator 100. If the lung volume module 117 does not determine a net negative volume with increasing magnitude, the lung volume module 117 continues to monitor for the net negative volume with increasing magnitude until a net negative volume change is detected or until an inspiration is delivered by the ventilator 100.

Ventilators 100, depending on their mode of operation, may trigger automatically and/or in response to a detected change in a ventilator 100 and/or patient parameter. The trigger module 115 receives and/or determines one or more inspiration trigger thresholds. In some embodiments, the trigger module 115 receives an inspiration trigger threshold from operator input. In other embodiments, the trigger module 115 determines an inspiration trigger threshold based on ventilator and/or patient parameters. During exhalation, in one embodiment, the trigger module 115 monitors ventilator and/or patient parameters and compares these parameters to one or more inspiration trigger thresholds to determine if the parameters meet and/or exceed the inspiration trigger thresholds. In some embodiments, the trigger module 115 receives the ventilator and/or patient parameter form other modules of the ventilator 100, such as the lung volume module 117 and the base flow estimator module 118.

Sensors 107 suitable for this detection may include any suitable sensing device as known by a person of skill in the art for a ventilator 100.

When a fixed base flow is undeterminable by the ventilator 100, the trigger module 115 utilizes at least one of the following trigger thresholds. In some embodiments, when a fixed base flow is undeterminable by the ventilator 100, the trigger module 115 triggers inspiration based on the first one of any of the following trigger thresholds to occur or to be exceeded.

In one embodiment, the ventilator 100 is preconfigured to deliver an inspiration after a predetermined amount of exhalation time to prevent a patient 150 from becoming under-ventilated. Accordingly, the predetermined amount of exhalation time (e.g., known as an apnea interval in some ventilators) is the trigger threshold in this embodiment. For example, the trigger module 115 will automatically trigger an inspiration after 20 seconds, 30 seconds, or 60 seconds of exhalation time. In some embodiments, the predetermined amount of time is determined by the clinician and/or ventilator 100 based on whether the patient 150 is an infant, child, adult, male, female, and/or suffering from a specific disease state.

In other embodiments, the trigger module 115 of the ventilator 100 may detect a flow-triggered event. If the ventilator 100 detects a slight drop in the base flow through the exhalation module during exhalation, this may indicate that the patient 150 is attempting to inspire. During flow triggering, the ventilator 100 is detecting a drop in base flow attributable to a slight redirection of gases into the patient's lungs (in response to a slightly negative pressure gradient as discussed above). However, in some scenarios, such as during BUV, the delivered base flow is undeterminable by the ventilator 100. Accordingly, in one embodiment, a flow-triggering method when a fixed base flow is undeterminable involves the trigger module 115 comparing a change in flow below the estimated base flow received from the base flow estimator module 118 to the flow trigger threshold.

In embodiments, the trigger module 115 utilizes a change in flow rate as an inspiration trigger threshold. For example, the inspiration trigger threshold may be a change in flow rate of −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable changes in flow rate may be utilized by the trigger module 115 for triggering an inspiration.

In some embodiments, the trigger module 115 receives a net negative change in lung volume from the lung volume module 117. As discussed above, the net negative change in lung volume is determined after the WDLV has passed zero or about zero after a decreasing trend in the WDLV (detection of a zero crossing). Accordingly, the net negative change in lung volume represents a decrease below a delivered base flow as discussed above. The trigger module 115 converts the received change in lung volume into a change in flow rate. In other embodiments, the lung volume module 117 converts the change in lung volume to a change in flow rate and then sends the change in flow rate to the trigger module 115 instead of sending the change in lung volume. Accordingly, in this embodiment, the trigger module 115 of the ventilator 100, when a fixed base flow is undeterminable by the ventilator 100, compares the converted change in lung volume received from the lung volume module 117 to the inspiration trigger threshold to determine a patient initiated inspiration trigger. In an alternative embodiment, the trigger module 115 converts the flow trigger threshold into a change in lung volume. Thus, in this embodiment, the trigger module 115 of the ventilator 100, when a fixed base flow is undeterminable by the ventilator 100, compares the converted change in lung volume received from the lung volume module 117 to the inspiration trigger threshold to determine a patient initiated inspiration trigger.

If the trigger module 115 determines that ventilator and/or patient parameters meet and/or exceed an inspiration trigger threshold during exhalation, the trigger module 115 instructs the inspiratory module 104 to deliver an inspiration, which effectively ends the exhalation phase. If the trigger module 115 determines that ventilator and/or patient parameters do not meet and/or exceed an inspiration trigger threshold during exhalation, the trigger module 115 continues to monitor the ventilator and/or patient parameters and compare them to a trigger threshold until the ventilator and/or patient parameters meet and/or exceed a trigger threshold.

Figure 2:
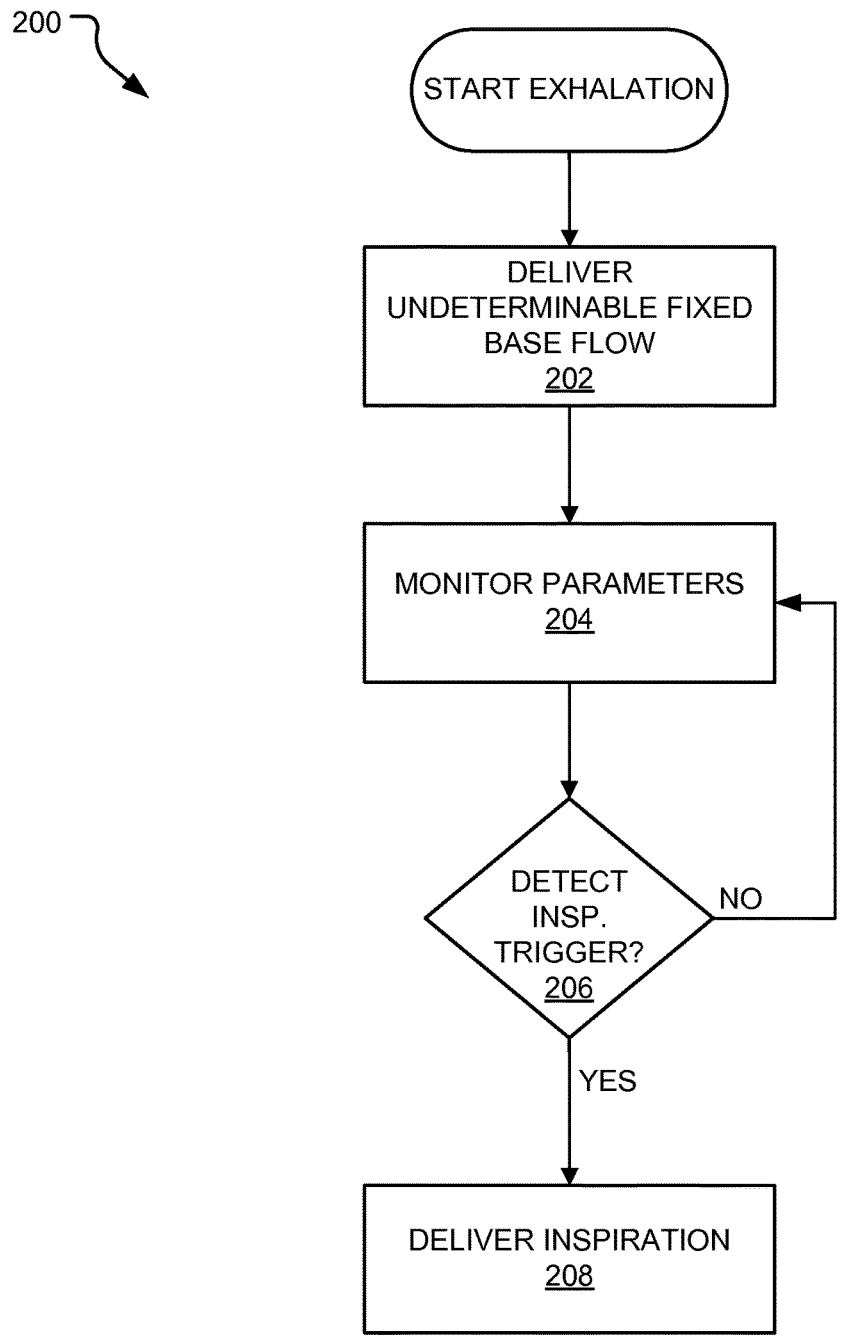
FIG. 2 illustrates an embodiment of a method for triggering inspiration during ventilation of a patient on a ventilator.

FIG. 2 illustrates an embodiment of a method 200 for triggering inspiration during ventilation of a patient on a ventilator. Method 200 begins at the start of exhalation. As illustrated, method 200 includes a deliver an undeterminable fixed base flow operation 202. During the deliver an undeterminable fixed base flow operation 202, the ventilator delivers a fixed but undeterminable base flow through the inspiratory limb. In some embodiments, a fixed base flow is indeterminable by the ventilator when at least one of the following conditions occur: an absence of an inspiratory flow sensor; a malfunction of the inspiratory flow sensor; a malfunction that prevents utilization of the inspiratory flow sensor; an inspiratory module malfunction; a malfunction that deactivates at least one of a data measurement subsystem and a data acquisition subsystem, and any other ventilator malfunction that prevents the ventilator from being able to measure inspiration flow. In some embodiments, during a malfunction, the ventilator is capable of delivering a fixed base flow by holding a back-up valve open in a fixed position on a bypass limb.

Further, method 200 includes a monitoring operation 204. During the monitoring operation 204, the ventilator monitors ventilator and/or patient parameters. As used herein ventilator parameters include all parameter determined by the operator and/or ventilator. As used herein patient parameters include any parameter that is not determined by the ventilator and/or operator. In some embodiments, the ventilator during the monitoring operation 204 monitors exhalation time, exhalation lung volume, exhalation flow rate, exhalation pressure, and/or a restricted period. Sensors suitable for this detection may include any suitable sensing device as known by a person of skill in the art for a ventilator, such as an expiration flow sensor.

Further, method 200 includes decision operation 206. During the decision operation 206, the ventilator determines if an inspiratory trigger is detected. An inspiratory trigger is detected when a monitored patient and/or ventilator parameter exceeds an inspiratory trigger threshold. In some embodiments, the inspiration trigger threshold is received from operator input. In other embodiments, the inspiration trigger threshold is based on ventilator and/or patient parameters.

In one embodiment, the inspiratory trigger threshold is at least one of the following inspiration trigger thresholds. In some embodiments, the ventilator during decision operation 206 determines a patient initiated inspiration based on the first one of any of the following trigger thresholds to occur or to be exceeded.

In one embodiment, the ventilator may be preconfigured to deliver an inspiration after a predetermined amount of exhalation time to prevent a patient from becoming under-ventilated. Accordingly, the predetermined amount of exhalation time is the trigger threshold in this embodiment. For example, the ventilator will automatically trigger an inspiration after 20 second, 30 seconds, or 60 seconds of exhalation time during decision operation 206. In some embodiments, the predetermined amount of time is determined by the clinician and/or ventilator based on whether the patient is an infant, child, adult, male, female, and/or suffering from a specific disease state. In some embodiments, a net negative change in flow rate below a delivered base flow is the inspiration trigger threshold. For example, the inspiration trigger threshold may be a change in flow rate of −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable change in flow rate below the delivered base flow may be utilized by the ventilator as an inspiration trigger threshold during decision operation 206.

A slight drop in the base flow through the exhalation module during exhalation may indicate that a patient is attempting to inspire. A drop in base flow is attributable to a redirection of gases into the patient's lungs (in response to a slightly negative pressure gradient as discussed above). However, because the fixed base flow is undeterminable, a change in flow rate below the base flow is not detectable. Accordingly, the ventilator during decision operation 206 may compare a change in flow rate below an estimated base flow to the flow trigger threshold. The method for estimating base flow is described below in method 400 and illustrated in FIGS. 4 and/or 5.

In some embodiments, the ventilator during decision operation 206 compares a change in a net negative lung volume after converted into a corresponding change in flow rate to a flow inspiration trigger threshold. The net negative change in lung volume is determined after a WDLV metric has passed through zero or about zero (or a slope≈0) after a decreasing trend (or negative slope) in the WDLV metric. Accordingly, the net negative change in lung volume represents a change that is below the delivered base flow. In other embodiments, the ventilator during decision operation 206 compares a change in lung volume to a flow inspiration trigger threshold converted into a change in lung volume. The method for determining a change in lung volume is described below in method 300 and illustrated in FIGS. 3A and 3B.

If the ventilator during decision operation 206 determines that an inspiration threshold has been met or exceeded, the ventilator selects to perform the deliver inspiration operation 208. If the ventilator during decision operation 206 determines that an inspiration trigger threshold has not been met or exceeded, the ventilator selects to perform monitoring operation 204 again.

Method 200 includes deliver inspiration operation 208. The ventilator during deliver inspiration operation 208 delivers inspiration to the patient and ends exhalation. The inspiration provided to the patient may be determined by the ventilator and/or patient parameters. For example, the delivered inspiration may be based on a selected breath type or ventilation mode, such as BUV.

In other embodiments, method 200 includes a display operation. The ventilator during the display operation displays any suitable information for display on a ventilator. In one embodiment, the display operation displays at least one of a WDLV, a net negative change in lung volume, an estimated base flow, an exhalation flow, a restricted period during which no inspiratory trigger is allowed, a trigger threshold, a sampling period for the WDLV and/or any other information known, received, or stored by the ventilator.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2.

In some embodiments, the ventilator system includes: means for delivering an undeterminable fixed base flow; monitoring ventilator and/or patient parameters, determining that an inspiration trigger threshold has been met or exceeded based on the monitored parameters; and delivering inspiration after the step of determining that the inspiration trigger threshold has been met or exceeded.

Figure 3A:
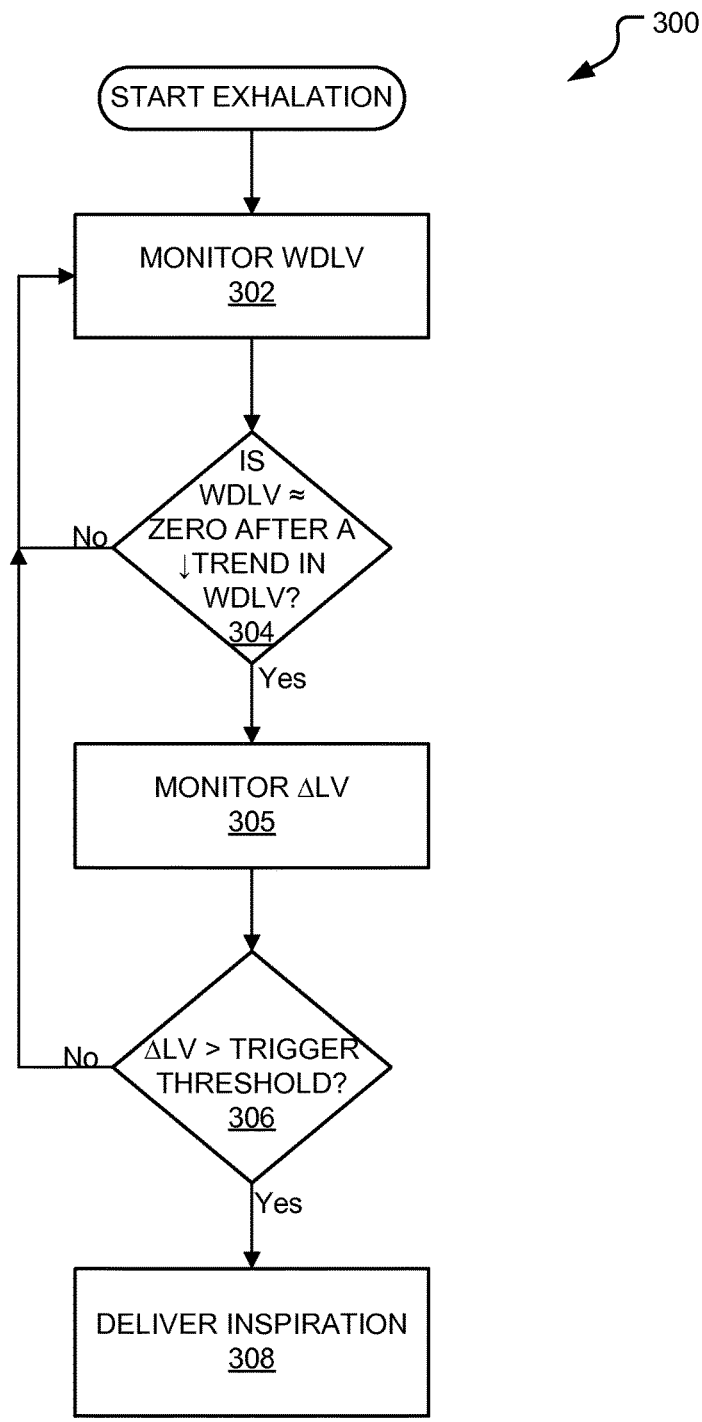
FIG. 3A illustrates an embodiment of a method for triggering inspiration during ventilation of a patient on a ventilator.
Figure 3B:
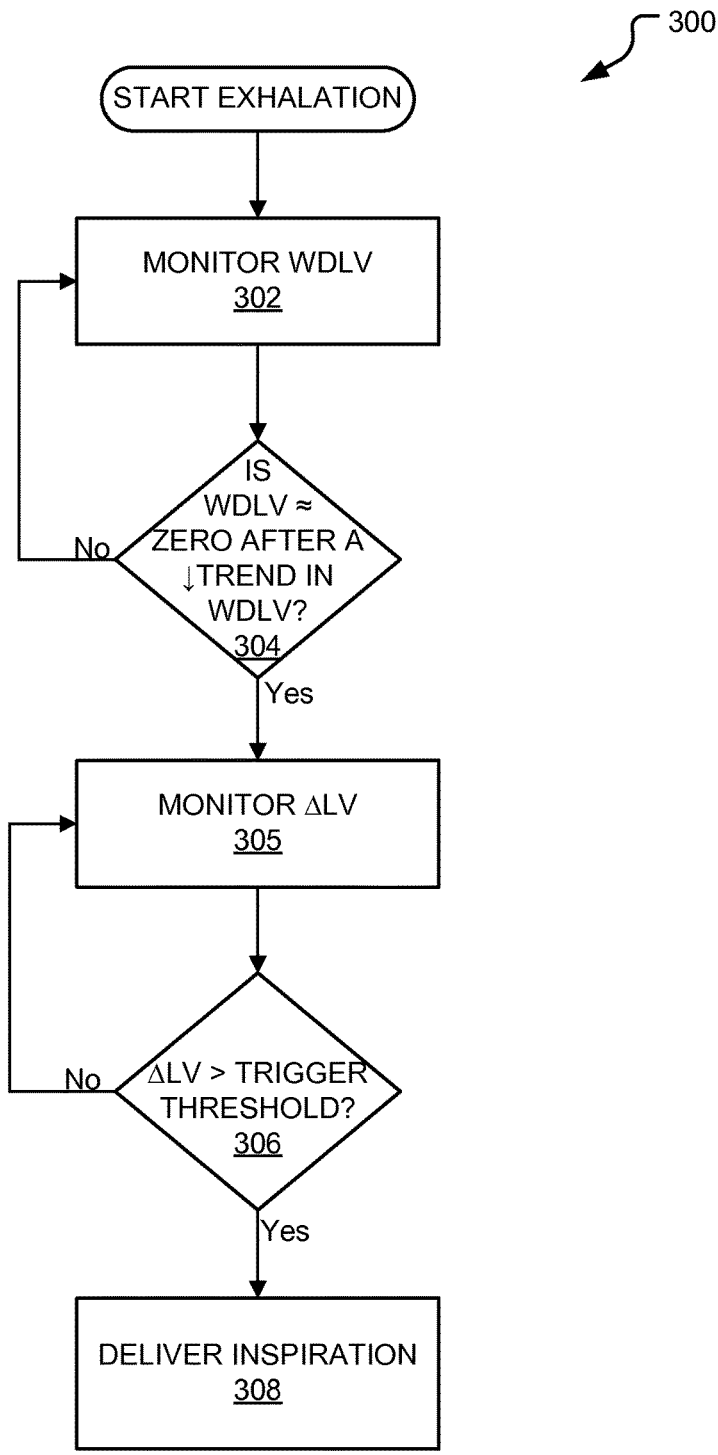
FIG. 3B illustrates an embodiment of a method for triggering inspiration during ventilation of a patient on a ventilator.

FIGS. 3A and 3B illustrate alternative embodiments of a method 300 for triggering inspiration during ventilation of a patient on a ventilator. Method 300 provides a method for triggering inspiration when a delivered base flow in the inspiratory limb is undeterminable by the ventilator. For example, the ventilator may not be able to determine the amount of base flow delivered through if the inspiration flow sensor and/or the inspiration flow module are malfunctioning. In another example, the ventilator may not be able to determine the amount of base flow delivered if the ventilator does not contain an inspiration flow sensor.

Method 300 begins at the start of exhalation. As illustrated in FIGS. 3A and 3B, method 300 includes a monitoring windowed differential lung volume (WDLV) operation 302. The ventilator during the monitoring WDLV operation 302 monitors a WDLV during exhalation. In some embodiments, the ventilator does not monitor the WDLV until after the restricted period. A WDLV comparison provides a progressive monitoring of differential volume changes into and out of the patient lung over a certain time window. By using the volume differential over windowed intervals, the sum of the fixed base flow rates cancel out as shown in the equations below:

$$WDLV = \Sigma_{j=n-i}^{j=n}(Qe(j)) - \Sigma_{j=n-2i-1}^{j=n-i-1}(Qe(j) - qd(j));$$

Therefore $$WDLV = \Sigma_{j=n-i}^{j=n}(Qe(j)) - \Sigma_{j=n-2i-1}^{j=n-i-1}(Qe(j))$$

and $$\Delta LV = WDLV * \Delta T.$$

WDLV=Differential Lung Volume over a window (w);
Qe=exhausted flow rate reading;
Qd=fixed delivered Base Flow;
n=discrete data sampling cycle number;
ΔLV=Differential lung volume;
ΔT=sampling period (sec).

Because the fixed base flow rate cancels out, there is no need to measure delivered flow or have an inspiratory flow sensor. For example, for a ventilator with a data sampling rate of 200 HZ (5 ms Computation cycles), a window of 5 cycles (25 ms) may be used (w=5, i=4).

Next, method 300 includes a first decision operation 304. During the first decision operation 304, the ventilator determines if the WDLV is zero or about zero after a decreasing trend in WDLV. The WDLV will have a positive magnitude (or slope) with an increasing trend during the initial phase of active exhalation as the patient's exhaled flow increases to its peak as illustrated in FIG. 5. As the exhaled flow starts decreasing after passing through its peak, the WDLV metric inflects and will have a negative magnitude (or slope) and demonstrate a decreasing trend toward zero as active exhalation is completed as illustrated in FIG. 5. The WDLV metric will be zero or about zero when the patient has finished exhalation and therefore the flow rate exiting the exhalation module would represent the delivered base flow (under no leak condition). Accordingly, monitoring the WDLV metric allows the ventilator to determine when a patient has finished active exhalation and entered stable exhalation. In some embodiments, the ventilator during first decision operation 304 determines that the WDLV metric is at zero or about zero after an increasing WDLV trend followed by a decreasing trend in WDLV.

If the ventilator during first decision operation 304 determines that the WDLV metric is not about zero after a decreasing trend, then the ventilator selects to perform monitoring WDLV operation 302. If the ventilator during first decision operation 304 determines that the WDLV metric is at zero or about zero (i.e., when the patient has finished exhaling), then the ventilator selects to perform monitoring changes in lung volume operation 305.

Next, method 300 performs a monitoring a change in lung volume operation 305. During the monitoring changes in lung volume operation 305, the ventilator monitors for changes in lung volume while the WDLV metric is at zero or about zero. By monitoring WDLV or changes in lung volume while the WDLV is at zero or about zero, if the patient initiates an inspiratory effort, a portion of the fixed base flow will move into the lung and the magnitude of the output flow reading (Qe) will decrease as illustrated in FIG. 5. Therefore, WDLV or ΔLV will indicate a net negative volume with increasing magnitude (−ΔLV=net volume into the lung). As discussed above a ΔLV is equal to the WDLV multiplied by computation cycle time. Accordingly, the ventilator will determine if a net negative volume with increasing magnitude occurred after the portion of exhalation in which the WDLV metric passed through zero or about zero. If the ventilator determines a net negative volume with increasing magnitude then this represents a change in flow below base flow.

As illustrated, method 300 includes a second decision operation 306. The ventilator during second decision operation 306 determines if a net negative change in lung volume with an increasing magnitude is equal to or greater than a trigger threshold.

When base flow is determinable, the ventilator triggers inspiration when the ventilator detects a slight drop in the base flow that meets or exceeds an inspiration trigger. During flow triggering, the ventilator is detecting a drop in base flow attributable to a slight redirection of gases into the patient's lungs (in response to a slightly negative pressure gradient as discussed above).

Accordingly, the ventilator during second decision operation 306 compares a net negative change in lung volume with increasing magnitude to an inspiration trigger threshold. In one embodiment, the ventilator converts the inspiration flow trigger threshold into volume over the corresponding time interval for the comparison to the change in lung volume. In an alternative embodiment, the ventilator converts the change in lung volume into a flow rate for comparison to the inspiration flow trigger threshold. If the ventilator determines that the converted net negative change in lung volume with increasing magnitude is greater than the inspiration flow trigger threshold, then the ventilator selects to perform delivery operation 308. If the ventilator determines that the converted net negative change in lung volume with increasing magnitude is not greater than the inspiration flow trigger threshold, then the ventilator selects to perform monitoring WDLV operation 302 in the next computational cycle as illustrated in FIG. 3A.

In an alternative embodiment, if the ventilator determines that the converted net negative change in lung volume with increasing magnitude is not greater than the inspiration flow trigger threshold, then the ventilator selects to perform monitoring changes in lung volume operation 306 in the next computational cycle instead of monitoring WDLV operation 302 as illustrated in FIG. 3B. Accordingly, in the embodiment illustrated in 3B, once the ventilator determines during first decision operation 304 that the WDLV metric is at zero or about zero, the ventilator does not perform the first decision operation 304 again until the next exhaled breath unlike the method shown in FIG. 3A. In other words, in the embodiment illustrated in 3B, if the ventilator determines that the converted net negative change in lung volume with increasing magnitude is not greater than the inspiration flow trigger threshold during second decision operation 306 in a computation cycle, the ventilator only performs the monitoring changes in lung volume operation 305 and second decision operation 306 in the next computation cycle of exhalation. For example, in the embodiment shown in FIG. 3A, the ventilator performs the monitoring WDLV operation 3A, the first decision operation 304, and the monitoring changes in lung volume operation 305 in the next computation cycle of exhalation after the computation cycle where the ventilator determined that the net negative change in lung volume with increasing magnitude is not greater than the inspiration flow trigger threshold during second decision operation 306.

In some embodiments the inspiration trigger threshold is a change in flow rate of −2 LPM, −3 LPM, −4 LPM, −5 LPM, −6 LPM, −7 LPM, and −8 LPM or is a range of a change in flow rate, such as a range of −3 LPM to −6 LPM or −4 LPM to −7 LPM. This list is exemplary only and is not meant to be limiting. Any suitable changes in flow rate may be utilized by the ventilator for triggering an inspiration.

Next, method 300 includes a delivery operation 308. During the delivery operation 308, the ventilator delivers inspiration to the patient ending exhalation. The inspiration provided by the ventilator to the patient may be determined by the ventilator and/or patient parameters. For example, the delivered inspiration may be based on a selected breath type or ventilation mode, such as BUV. Delivery operation 308 is similar to deliver inspiration operation 208 of method 200.

In other embodiments, a microprocessor-based ventilator that accesses a computer-readable medium having computer-executable instructions for performing the method of ventilating a patient with a ventilator is disclosed. This method includes repeatedly performing the steps disclosed in method 300 above and/or as illustrated in FIGS. 3A and 3B.

In some embodiments, the ventilator system includes: means for delivering a fixed base flow that is undeterminable; means for monitoring a windowed differential lung volume during exhalation; means for determining that the windowed differential lung volume is at about zero after a decreasing trend toward zero; and means for triggering inspiration based on the first of at least one of the following events to occur: a net negative change in lung volume with increasing magnitude is detected that is greater than an inspiratory trigger threshold directly after the step of determining that the windowed differential lung volume is about zero; and a predetermined amount of time expires.

Figure 4A:
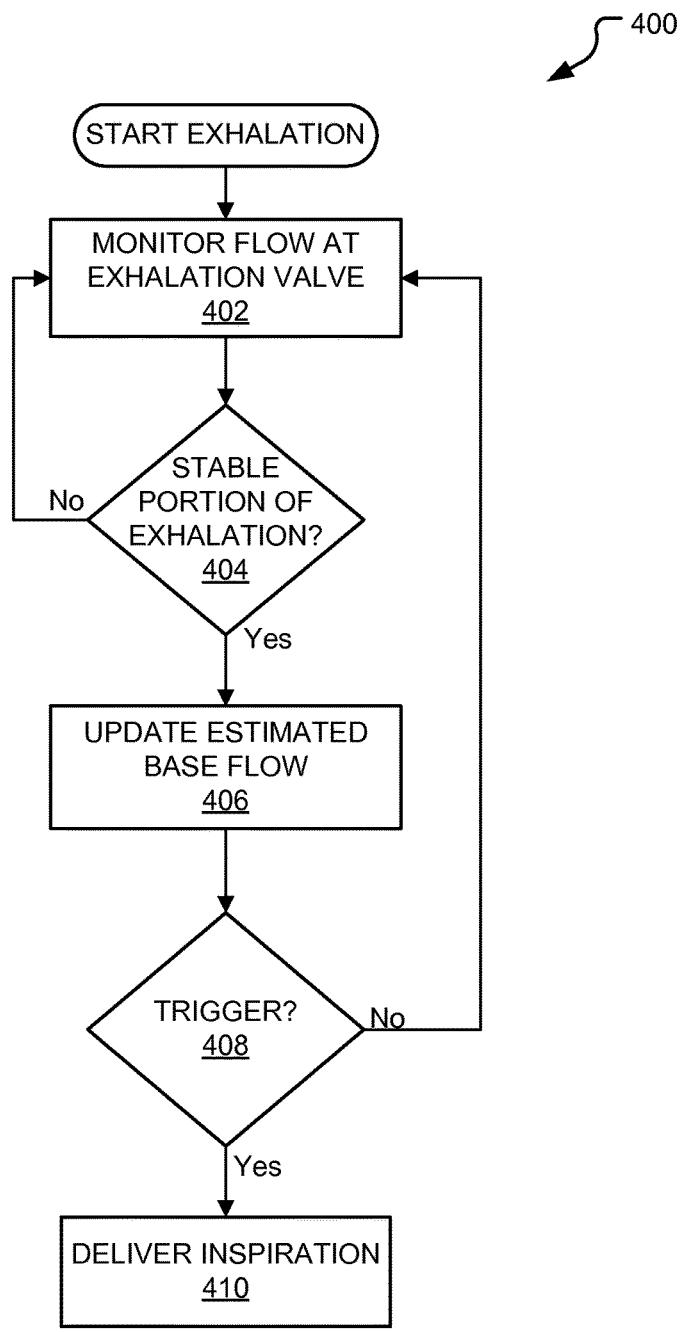
FIG. 4A illustrates an embodiment of a method for triggering inspiration during ventilation of a patient on a ventilator.
Figure 4B:
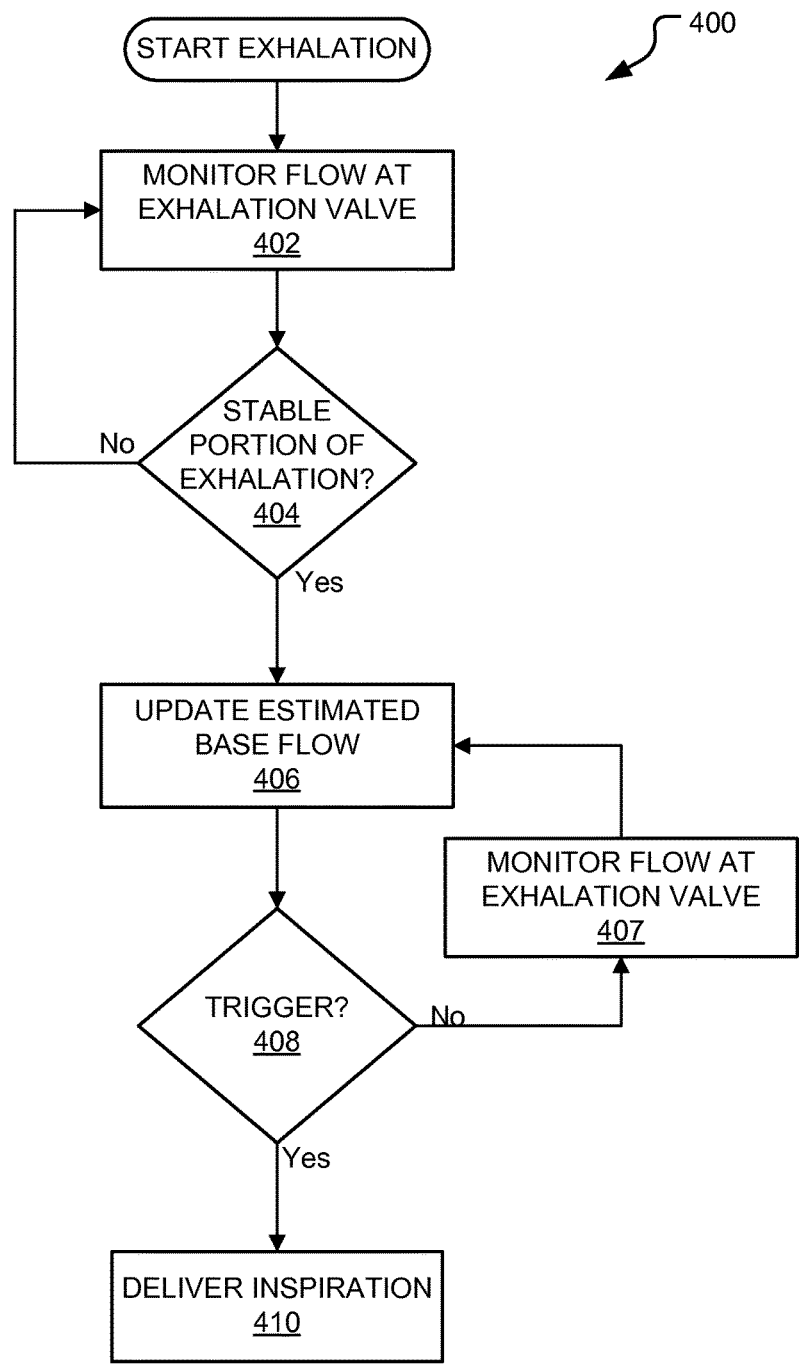
FIG. 4B illustrates an embodiment of a method for triggering inspiration during ventilation of a patient on a ventilator.

FIGS. 4A and 4B illustrate alternative embodiments of a method 400 for triggering inspiration during ventilation of a patient on a ventilator. Method 400 provides a method for triggering inspiration when a delivered base flow is undeterminable by the ventilator. In one embodiment, the ventilator may not be able to determine the amount of base flow delivered through the inspiratory limb if the inspiration flow sensor and/or the inspiration flow module are malfunctioning. In another example, the ventilator may not be able to determine the amount of base flow delivered through the inspiratory limb if the ventilator does not contain an inspiration flow sensor. For example, the ventilator cannot determine the fixed amount of delivered base flow during BUV.

Method 400 begins at the start of exhalation. As illustrated in FIG. 4, method 400 includes a monitoring operation 402. The ventilator during the monitoring operation 402 monitors exhalation flow and exhalation pressure. The ventilator does not monitor the exhalation flow and exhalation pressure until after the restricted period during which no inspiratory triggers are allowed. The ventilator may utilize any suitable sensors or measuring devices for determining the exhalation flow and exhalation pressure, such as an exhalation flow sensor and/or an exhalation pressure sensor.

In some embodiments, the ventilator monitors multiple exhalation pressure and exhalation flow readings in at least two different circular buffers for a set period during exhalation after the expiration of a restricted period. In one embodiment, ventilator utilizes exhalation flow and pressure readings in two 10-slot circular buffers beginning after the end of the restricted period. In this embodiment, the ventilator monitors the exhalation flow every computation cycle. In some embodiments, the computational cycle is every 5 ms.

Next, method 400 includes a stable portion decision operation 404. During the stable portion decision operation 404, the ventilator determines if the patient is in the stable portion of exhalation. In one embodiment, the stable portion of exhalation is the portion of exhalation when a patient is contributing very little or no flow through the patient circuit and is prior to the beginning of inspiration as illustrated in FIG. 5. In another embodiment, the ventilator simulates a stable portion of exhalation during a transition period. During the transition period, the ventilator opens the exhalation valve fully and delivers a fixed base flow into the patient circuit in an attempt to simulate a stable portion of exhalation in the ventilator tubing system. In some embodiments, the ventilator simulates a stable portion of exhalation or executes a transition period after a determining a fault, such as a malfunction inspiration flow sensor, and before ventilating a patient in a back-up ventilation mode, such as BUV.

If the ventilator simulates the stable portion of exhalation, the ventilator knows exactly when the stable portion of exhalation occurs because the stable portion of exhalation is controlled and/or determined by the ventilator. When the ventilator does not simulate the stable portion of exhalation, the ventilator must determine when the patient enters the stable portion of exhalation during ventilation. In order to determine the stable portion of exhalation, the ventilator utilizes the monitored exhalation pressure and exhalation flow. For example, the ventilator determines if the difference between the maximum exhalation pressure and the minimum exhalation pressure is less that 1.5 cm of $H_2O$ ((Max $(P_e)$–Min$(P_e)$)<1.5 cm $H_2O$) and determines if the difference between maximum exhalation flow and minimum exhalation flow is less than 1.5 LPM ((Max$(Q_e)$–Min$(Q_e)$)<1.5 LPM) for a defined interval during exhalation. If the difference between the maximum exhalation pressure and the minimum exhalation pressure is less that 1.5 cm of $H_2O$ and the difference between maximum exhalation flow and minimum exhalation flow is less than 1.5 LPM for a defined interval, then the ventilator determines that the patient is in the stable portion of exhalation. If the difference between the maximum exhalation pressure and the minimum exhalation pressure is not less than 1.5 cm of $H_2O$ and/or the difference between maximum exhalation flow and minimum exhalation flow is not less than 1.5 LPM for either computation cycle, then the ventilator determines that the patient is not in the stable portion of exhalation.

The embodiments, discussed above are merely exemplary and are not meant to be limiting. Any suitable method for determining a stable period of exhalation may be utilized by the present disclosure.

If the ventilator during stable portion decision operation 404 determines that the patient has entered the stable portion of exhalation, the ventilator selects to perform the update estimated base flow operation 406. If the ventilator during stable portion decision operation 404 determines that the patient has not entered the stable portion of exhalation, the ventilator selects to perform monitoring operation 402.

Method 400 also includes an update operation 406. During the update operation 406, the ventilator determines an estimated base flow or updates a previously calculated estimated base flow with a more current estimated base flow. If the ventilator simulated the stable portion of exhalation, the ventilator estimates base flow by taking a predetermined number of exhalation flow measurements and then averaging the exhalation flow measurements. The averaged estimated flow measurement is then utilized as the estimated base flow by the ventilator. In some embodiments, during the ventilator simulated stable portion of exhalation, the pressure in the accumulator is also measured to determine an estimated accumulator pressure. In some embodiments, the ventilator simulates a stable portion of exhalation in the ventilator tubing system prior to the beginning of ventilation in a back-up mode, such as BUV. Accordingly, in some embodiments, the first estimated base flow utilized, such as an initializing base flow, during method 400 is from the transition period where the ventilator simulates a stable base flow through the ventilator tubing system.

If the stable portion of exhalation was not simulated by the ventilator, the ventilator determines the estimated base flow by taking the last or most recently measured circular buffer and averaging all of the exhalation flows. For example, if the ventilator utilized a 10-slot circular buffer, the last ten measured exhalation flows are summed and then divided by ten providing an averaged exhalation flow. The ventilator utilizes the determined averaged exhalation flow as the estimated base flow. In some embodiments, the ventilator continuously updates the estimated base flow during exhalation throughout ventilation with an undeterminable fixed base flow.

Next, method 400 includes a trigger decision operation 408. During the trigger decision operation 408, the ventilator determines if a change in exhalation flow rate below the estimated base flow is equal to or greater than a trigger threshold.

When base flow is determinable, the ventilator triggers inspiration when the ventilator detects a slight drop below the base flow during exhalation. During flow triggering, the detected drop in base flow by the ventilator is attributable to a slight redirection of gases into the patient's lungs (in response to a slightly negative pressure gradient as discussed above). However, in some scenarios, such as during method 400, the delivered base flow is undeterminable by the ventilator. Accordingly, the ventilator during trigger decision operation 408 compares a detected change in exhalation flow below the estimated base flow during the stable portion of exhalation to the flow trigger threshold. In some embodiments, the inspiration trigger threshold may be a change in flow rate of −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable changes in flow rate may be utilized by the ventilator for triggering an inspiration.

If the ventilator determines that change in exhalation flow below the base flow is equal to or greater than the inspiration flow trigger threshold, then the ventilator selects to perform deliver operation 410. If the ventilator determines that change in exhalation flow below the base flow is not equal to or greater than the inspiration flow trigger threshold, then the ventilator selects to perform monitoring operation 402 in the next computational cycle.

In alternative embodiments, as illustrated in FIG. 4B, if the ventilator determines that a change in exhalation flow below the base flow is not equal to or greater than the inspiration flow trigger threshold, then the ventilator selects to perform monitoring operation 407 in the next computational cycle. Accordingly, in the embodiment illustrated in 4B, once the ventilator determines during stable portion decision operation 404 that the patient has entered the stable portion of exhalation, the ventilator does not perform the stable portion decision operation 404 again until the next exhaled breath unlike the method shown in FIG. 4A. In other words, in the embodiment illustrated in 4B, if the ventilator determines that a change in exhalation flow below the base flow is not equal to or greater than the inspiration flow trigger threshold during trigger decision operation 408 in a computation cycle, the ventilator only performs the monitoring operation 407 and trigger decision operation 408 in the next computation cycle of exhalation. For example, in the embodiment shown in FIG. 4A, the ventilator performs the monitoring operation 402, the stable portion decision operation 404, and the update operation 406 in the next computation cycle of exhalation after the computation cycle where the ventilator determined that a change in exhalation flow below the base flow is not equal to or greater than the inspiration flow trigger threshold during trigger decision operation 408.

In some embodiments, method 400 performs a monitoring flow operation 407. During the monitoring flow operation 407, the ventilator monitors exhalation flow during the stable portion of exhalation. Further, the ventilator monitors for any changes in flow below the estimated base flow during the monitoring flow operation 407. The ventilator may utilize any suitable sensors or measuring devices for determining the exhalation flow, such as an exhalation flow sensor and/or an exhalation pressure sensor. The monitoring flow operation 407 is similar to monitoring flow operation 402 except that the stable portion of exhalation has already been established and monitoring flow operation 407 is located in a different position in the flow of method 400.

As illustrated, method 400 includes a deliver operation 410. During the deliver operation 410, the ventilator delivers inspiration to the patient ending exhalation. The inspiration provided by the ventilator to the patient may be determined by the ventilator and/or patient parameters. For example, the delivered inspiration may be based on a selected breath type or ventilation mode, such as BUV. Deliver operation 410 is similar to delivery operation 308 of method 300 and deliver inspiration operation 208 of method 200.

In other embodiments, a microprocessor-based ventilator that accesses a computer-readable medium having computer-executable instructions for performing the method of ventilating a patient with a ventilator is disclosed. This method includes repeatedly performing the steps disclosed in method 400 above and/or as illustrated in FIGS. 4 and 5.

In some embodiments, the ventilator system includes: means for delivering a fixed base flow that is undeterminable; means for determining a stable portion of exhalation; means for monitoring exhalation flow during the stable portion of exhalation; means for estimating a base flow based on the exhalation flow monitored during the stable portion of exhalation; and means for triggering inspiration based on the first of at least one of the following events to occur: a flow derivation based on the estimated base flow is detected that is greater than the inspiratory trigger threshold during the stable portion of exhalation; and expiration of a predetermined amount of time.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator, comprising:
   delivering a fixed base flow;
   determining a stable portion of exhalation;
   monitoring an exhalation flow during the stable portion of exhalation and in an absence of a determinable inspiratory flow;
   estimating a base flow based on the exhalation flow monitored during the stable portion of exhalation;
   determining that a flow derivation based on the estimated base flow is greater than an inspiratory trigger threshold during the stable portion of exhalation; and triggering inspiration based on the determining that the flow derivation is greater than the inspiratory trigger threshold.

2. The method of claim 1, wherein the inspiration flow is undeterminable because of at least one of the following malfunctions:
a malfunction of an inspiratory flow sensor;
a malfunction that prevents utilization of the inspiratory flow sensor
an inspiratory module malfunction; and
a malfunction that deactivates at least one of a data measurement subsystem and a data acquisition subsystem.

3. The method of claim 1, wherein the inspiration flow is undeterminable because of an absence of an inspiratory flow sensor.

4. The method of claim 1, wherein the stable portion of exhalation is a time during exhalation when a slope of patient exhalation flow is about zero.

5. The method of claim 1, wherein the stable portion of exhalation occurs when $$(Max(P_e)-Min(P_e))<1.5 \text{ cm } H_2O \text{ and } (Max(Q_e)-Min(Q_e))<1.5 \text{ LPM) for each computation cycle,}$$

wherein $Max(P_e)$ is a maximum exhalation pressure, $Min(P_e)$ is a minimum exhalation pressure, $Max(Q_e)$ is a maximum exhalation flow, and $Min(Q_e)$ is a minimum exhalation flow.

6. The method of claim 1, wherein the inspiratory trigger threshold is a change in flow rate.

7. The method of claim 1, wherein a net negative change in lung volume is converted into flow rate for comparison to the inspiratory trigger threshold.

8. The method of claim 7, wherein the inspiratory trigger threshold is a change of at least 5 LPM.

9. A ventilator system comprising:
a pressure generating system adapted to generate a flow of breathing gas;
wherein the pressure generating system delivers a fixed base flow,
a ventilation tubing system including a patient interface for connecting the pressure generating system to a patient;
at least one sensor operatively coupled to at least one of the pressure generating system, the patient, and the ventilation tubing system, wherein the at least one sensor is capable of generating an output indicative of an exhalation flow;
a base flow estimator module for determining a stable portion of exhalation, monitoring the exhalation flow during the stable portion of exhalation based on the output, and for estimating a base flow based on the exhalation flow monitored during the stable portion of exhalation and in an absence of determinable inspiratory flow; and
a trigger module that determines that a flow derivation based on an estimated base flow is greater than an inspiratory trigger threshold and then triggers inspiration.

10. The ventilator system of claim 9, wherein the stable portion of exhalation occurs when $$(Max(P_e)-Min(P_e))<1.5 \text{ cm } H_2O \text{ and } (Max(Q_e)-Min(Q_e))<1.5 \text{ LPM) for each computation cycle, and}$$

wherein $Max(P_e)$ is a maximum exhalation pressure, $Min(P_e)$ is a minimum exhalation pressure, $Max(Q_e)$ is a maximum exhalation flow, and $Min(Q_e)$ is a minimum exhalation flow.

11. The ventilator system of claim 9, further comprising:
a display in communication with at least one of a lung volume module and the trigger module, the display displays at least one of a net negative change in lung volume, the estimated base flow, the exhalation flow, a restricted period, and a trigger threshold.

12. The ventilator system of claim 9, wherein the inspiration flow is undeterminable because of an absence of an inspiratory flow sensor.

13. The ventilator system of claim 9, wherein the inspiration flow is undeterminable because of at least one of the following malfunctions:
a malfunction of an inspiratory flow sensor;
a malfunction that prevents utilization of the inspiratory flow sensor
an inspiratory module malfunction; and
a malfunction that deactivates at least one of a data measurement subsystem and a data acquisition subsystem.

14. The ventilator system of claim 9, wherein the inspiratory trigger threshold is a change in flow rate.

15. The ventilator system of claim 14, wherein a net negative change in lung volume is converted into flow rate for comparison to the inspiratory trigger threshold.

16. The ventilator system of claim 15, wherein the inspiratory trigger threshold is a change of at least 5 LPM.

17. A computer-readable medium having computer-executable instructions for ventilating a patient with a ventilator, the instructions comprising:
deliver a fixed base flow that is undeterminable;
determine a stable portion of exhalation;
monitor an exhalation flow during the stable portion of exhalation;
estimate a base flow based on the exhalation flow monitored during the stable portion of exhalation;
determine that a flow derivation based on the estimated base flow is greater than an inspiratory trigger threshold during the stable portion of exhalation; and
trigger inspiration based on the determining that the flow derivation is greater than the inspiratory trigger threshold.

18. A computer-readable medium having computer-executable instructions for ventilating a patient with a ventilator, the instructions comprising:
deliver a fixed base flow that is undeterminable;
monitor a windowed differential lung volume during exhalation;
determine that the windowed differential lung volume is at about zero after a decreasing trend toward zero; and
trigger inspiration based on the first of at least one of the following events to occur:
a net negative change in lung volume with increasing magnitude is detected that is greater than an inspiratory trigger threshold directly after the step of determining that the windowed differential lung volume is about zero; and
a predetermined amount of time expires.

19. A computer-readable medium having computer-executable instructions for ventilating a patient with a ventilator, instructions comprising:
deliver a fixed base flow that is undeterminable;
determine a stable portion of exhalation;

monitor an exhalation flow during the stable portion of exhalation;
estimate a base flow based on the exhalation flow monitored during the stable portion of exhalation; and
trigger inspiration based on the first of at least one of the following events to occur:
  a flow derivation based on the estimated base flow is detected that is greater than an inspiratory trigger threshold during the stable portion of exhalation; and
expiration of a predetermined amount of time.

* * * * *